United States Patent
Hinds, Jr. et al.

(10) Patent No.: US 10,662,153 B2
(45) Date of Patent: May 26, 2020

(54) THIN MOLECULES FOR THE TREATMENT OF OBESITY AND TYPE II DIABETES

(71) Applicant: The University of Toledo, Toledo, OH (US)

(72) Inventors: Terry D. Hinds, Jr., Toledo, OH (US); David E. Stec, Toledo, OH (US); Christopher J. Trabbic, Toledo, OH (US)

(73) Assignee: The University of Toledo, Toledo, OH (US)

( * ) Notice: Subject to any disclaimer, the term of this patent is extended or adjusted under 35 U.S.C. 154(b) by 0 days.

(21) Appl. No.: 16/078,254

(22) PCT Filed: Feb. 27, 2017

(86) PCT No.: PCT/US2017/019606
§ 371 (c)(1),
(2) Date: Aug. 21, 2018

(87) PCT Pub. No.: WO2017/151469
PCT Pub. Date: Sep. 8, 2017

(65) Prior Publication Data
US 2019/0047952 A1    Feb. 14, 2019

Related U.S. Application Data

(60) Provisional application No. 62/301,134, filed on Feb. 29, 2016.

(51) Int. Cl.
*A61K 31/4025*   (2006.01)
*A61K 31/4015*   (2006.01)
*C07D 403/02*   (2006.01)
*C07D 207/44*   (2006.01)
*A61P 3/04*   (2006.01)
*A61P 3/10*   (2006.01)

(52) U.S. Cl.
CPC ............. *C07D 207/44* (2013.01); *A61P 3/04* (2018.01); *A61P 3/10* (2018.01)

(58) Field of Classification Search
CPC ............ A61K 31/4025; A61K 31/4015; C07D 403/02; C07D 207/44; A61P 3/04; A61P 3/10
USPC .......................... 514/422, 424; 548/518, 543
See application file for complete search history.

(56) References Cited

PUBLICATIONS

Kufer, W. and H. Scheer, "The diazo reaction of Bilirubin: Structure of the yellow products" Tetrahedron (1983), 39 (11), pp. 1887-1892. (Year: 1983).*

* cited by examiner

*Primary Examiner* — Matthew P Coughlin
*Assistant Examiner* — Sagar Patel
(74) *Attorney, Agent, or Firm* — MacMillan, Sobanski & Todd, LLC

(57) ABSTRACT

Thin molecules, compounds producible by cleaving bilirubin at its methylene site in the center of the molecule, methods of making the same, and methods of using the same, are described.

4 Claims, 20 Drawing Sheets
(12 of 20 Drawing Sheet(s) Filed in Color)

THIN MOLECULES FOR THE TREATMENT OF OBESITY AND TYPE II DIABETES

RELATED APPLICATIONS

This application claims priority to U.S. Provisional Application Ser. No. 62/301,134 filed under 35 U.S.C. § 111 (b) on Feb. 29, 2016, the disclosure of which is incorporated herein by reference in its entirety.

STATEMENT REGARDING FEDERALLY SPONSORED RESEARCH

This invention was made with no government support. The government has no rights in this invention.

BACKGROUND OF THE INVENTION

Obesity is a major public health concern, with an estimated total number of overweight and obese individuals exceeding 150 million people in the U.S. In obesity, during adipose tissue expansion, pre-adipocytes differentiate to adipocytes with increased levels of reactive oxygen species (ROS) and free fatty acids. There are also a decrease in glucose uptake and changes in adipose tissue-derived hormones (adipokines), including an increase in inflammatory cytokines. All of these events are associated with the development of non-insulin dependent type II diabetes. Therefore, obesity and its associated risk factors are a prelude to the development of type II diabetes and its clinical manifestations such as hypertension.

Moderate plasma hyperbilirubinemia may protect against obesity and type II diabetes. Large population studies have demonstrated that physiologically elevated levels of serum bilirubin (Gilbert's syndrome) protect against the development of diabetes and the metabolic syndrome. It has been demonstrated that increased serum bilirubin levels protect against cardiovascular and metabolic diseases such as obesity and diabetes. Bilirubin is a potent antioxidant, and the beneficial actions of moderate increases in plasma bilirubin have been thought to be due to the antioxidant effects of this bile pigment. It is evident that adipocyte dysfunction and dysregulation of adipocytokines directly contributes to diabetes. Incerased bilirubin levels are positively associated with a leaner phenotype, and are protective of the vasculature system. However, there is a gap of knowledge for the precise molecular mechanisms by which bilirubin protects against diabetes and obesity. Beyond functioning as an antioxidant, bilirubin has no known physiologic function.

Bilirubin is a breakdown product of heme catabolism from hemoglobin, a critical element of red blood cells. At normal concentrations in mammals, unconjugated bilirubin is an efficient scavenger of singlet oxygen and acts as an antioxidant. Water-insoluble unconjugated bilirubin normally travels through the bloodstream to the liver, where it is converted into a water-soluble, conjugated form by the uridine diphosphate glucuronyltransferase (UGT) system and then excreted into bile. Mutations in the UGT system result in elevated plasma levels of unconjugated bilirubin.

Gilbert's syndrome (GS) is the most common hereditary cause of hyperbilirubinemia, affecting approximately 5% to 10% of the population. GS is the result of reduced activity of the UGT enzyme, UGT1A1, resulting in higher plasma bilirubin levels. GS patients exhibiting mildly elevated levels of bilirubin have been found to have a reduced risk of coronary artery disease (CAD) and a lower contingency for future heart disease. Hypertensive patients with established CAD have significantly lower bilirubin levels, which has also been shown in diabetic patients with CAD. Short-term weight loss in obese high-risk cardiovascular patients has been investigated, and it was found that bilirubin increased as body weight decreased. Bilirubin may be particularly effective in reducing adiposity since it readily enters the lipid environment. This may serve to protect patients with the metabolic syndrome, as it was shown that higher bilirubin levels were paralleled with lower visceral obesity. This correlates with the observation that obese patients with elevated insulin and visceral adiposity have decreased levels of bilirubin. GS patients have improved adipocyte function and vascular protection. However, the effects of bilirubin on adipocyte function have not been investigated.

Type 2 diabetes accounts for the vast majority of the 25.8 million diabetes cases in the U.S. More than 90% of type II diabetics are overweight or obese. To date, no drug has demonstrated sustainable efficacy in the treatment of type II diabetes. Therefore, it would be advantageous to develop further knowledge of the molecular mechanisms by which bilirubin protects against diabetes and obesity so as to develop treatments for type II diabetes.

SUMMARY OF THE INVENTION

Provided is a compound comprising a Formula A or Formula B:

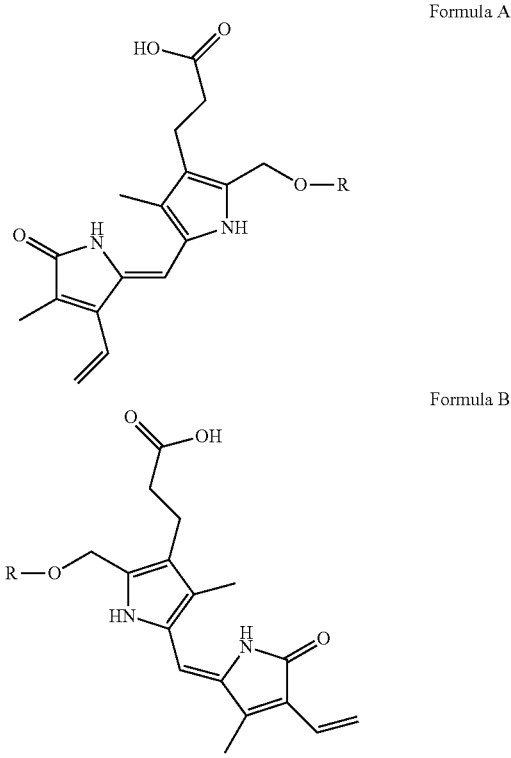

wherein R is selected from the group consisting of hydrogen and substituted or substituted $C_1$-$C_6$ alkyl. Also provided are salts, stereoisomers, racemates, prodrugs, solvates, and hydrates of the compound. In certain embodiments, R is methyl, ethyl, propyl, butyl, or pentyl. In certain embodiments, the compound is present in a mixture of Formula A and Formula B.

Also provided is a method of making a compound of Formula A or Formula B, the method comprising cleaving bilirubin in a cosolvent to produce a mixture of regioisomeric compounds of Formula A and Formula B, where R is determined by the cosolvent. In certain embodiments, the cleaving comprises a diazotization reaction on a methylene site of bilirubin, followed by nucleophilic displacement with the cosolvent. In particular embodiments, the diazotization reaction comprises reacting bilirubin with a diazotization reagent. In particular embodiments, the diazotization reagent comprises sodium nitrite. In particular embodiments, the cosolvent is a $C_1$-$C_6$ alkanol. In particular embodiments, the cosolvent is methanol, ethanol, or water. Also provided are the products of the method.

Also provided is a pharmaceutical composition comprising an effective amount of a compound described herein, and a pharmaceutically acceptable carrier, diluent, or adjuvant.

Also provided is a method of treating obesity or type II diabetes, the method comprising administering an effective amount of a compound described herein to a subject in need thereof and treating obesity or type II diabetes. In certain embodiments, the subject is a human subject.

Also provided is a method of activating PPARα in a subject, the method comprising administering an effective amount of a compound described herein to a subject and activating PPARα in the subject. In certain embodiments, the subject is a human subject.

Also provided is a method of determining coverage of health insurance reimbursement or payments, the method comprising denying coverage or reimbursement for a treatment, wherein the treatment comprises a compound described herein.

Also provided is a kit for making a thin molecule, the kit comprising a first container housing a diazotization reagent, and a second container housing bilirubin. In certain embodiments, the kit further comprises a cosolvent. In certain embodiments, the kit further comprises a pharmaceutically acceptable carrier, diluent, or adjuvant.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

FIG. 1A shows the structures of bilirubin and PPARα ligands WY-14,643 and fenofibrate. Highlighted in yellow are the believed PPAR binding region for bilirubin, with similarities to the PPARα ligands WY-14,643 and fenofibrate. FIG. 1B shows arachidonic acid, which is the precursor for CYP epoxygenase (2C and 2J) production of 5,6-, 8,9-, 11,12-, and 14,15-epoxyeicosatrienoic acids (EETs).

FIG. 2A shows bilirubin docked into PPARα binding pocket. FIG. 2B shows bilirubin binds in the same site occupied by the known PPARα ligand GW735. Bilirubin and the ligand are depicted in green and magenta carbon skeleton, respectively.

(FIG. 3C.) ****, $p<0.0001$ (versus 0 μM Veh); $ and ^^, $p<0.001$ (versus 0 μM BV and Feno, respectively); (±S.E.; n=4).

FIG. 4A shows a western blot of PPARα and HSP90 in lentiviral overexpression of PPARα and vector in 3T3-L1 cells. Bilirubin or WY 14,643 linked sepharose resins were used to determine direct binding to PPARα. (FIG. 4B.) The PPARα overexpression and vector 3T3-L1 cells were treated for 24 hours with biliverdin (BV) (50 μM), WY 14,643 (WY) (50 μM), or fenofibrate (Feno) (50 μM). (FIG. 4C.) RNA was extracted and CD36, CPT1, and FGF21 expression was measured by Real-time PCR. ***, $p<0.001$ (versus veh 3T3-Vector); ^, $p<0.05$ (versus veh 3T3-PPARα); ^^, $p<0.01$ (versus veh 3T3-PPARα); ^^^, $p<0.001$ (versus veh 3T3-PPARα); $, $p<0.05$ (versus WY 3T3-PPARα); $$, $p<0.01$ (versus WY 3T3-PPARα); #, $p<0.05$ (versus BV 3T3-PPARα); (±S.E.; n=3). The mouse hepa1c1c7 liver cells overexpressing PPARα were treated in dialyzed FBS for 24 hours with biliverdin (BV) (50 μM), WY 14,643 (WY) (50 μM), or fenofibrate (Feno) (50 μM). (FIG. 4D.) RNA was extracted and mRNA expression was measured by Real-time PCR. (FIG. 4E.) ^, $p<0.05$, ^^, $p<0.01$, and ^^^, $p<0.001$ (versus veh 3T3-PPARα); $, $p<0.05$, $$, $p<0.01$, $$$, $p<0.001$, $$$$, $p<0.0001$ (versus WY 3T3-PPARα); ###, $p<0.01$, #, $p<0.01$, ####, $p<0.0001$ (versus BV 3T3-PPARα); (±S.E.; n=3).

(FIG. 5A.) *, $p<0.05$; , $p<0.01$; *, $p<0.001$; **, $p<0.0001$ (versus Ctrl); ^^, $p<0.05$ (versus 10 μM WY); $, $p<0.05$ (versus 10 μM feno) (±S.E.; n=3). Lipid accumulation was measured in 3T3-L1 cells that were differentiated into mature adipocytes treated with vehicle (Ctrl), biliverdin (50 μM), WY 14,643 (50 μM), or fenofibrate (50 μM) over the 9 day protocol and Real-time PCR analysis of PPARγ2, C/EBPα, FAS, and CPT1. (FIG. 5B.) (versus Ctrl) , $p<0.01$; *, $p<0.001$; **, $p<0.0001$; (versus 50 μM WY) #, $p<0.05$; ##, $p<0.001$; (versus 50 μM feno) $, $p<0.001$ (±S.E.; n=3).

a, p<0.05 (KO versus WT Ctrl); b, p<0.05 (WT FF or BR treated versus WT Ctrl); c, p<0.05 (WT BR treated versus WT FF treated); d, p<0.05 (KO FF treated versus WT FF); e, p<0.05 (KO BR treated versus WT BR) (±S.E.; n=5).

Figure 8A:
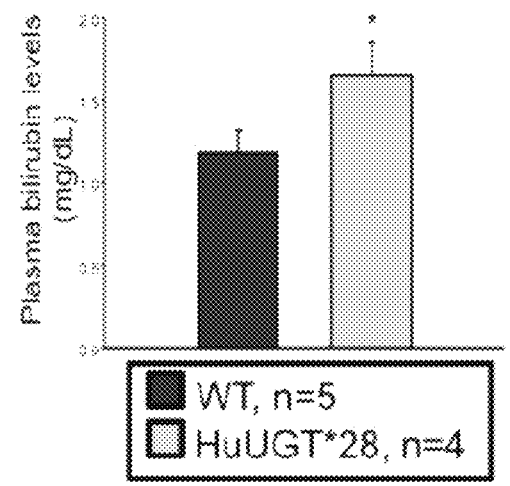
Figure 8B:
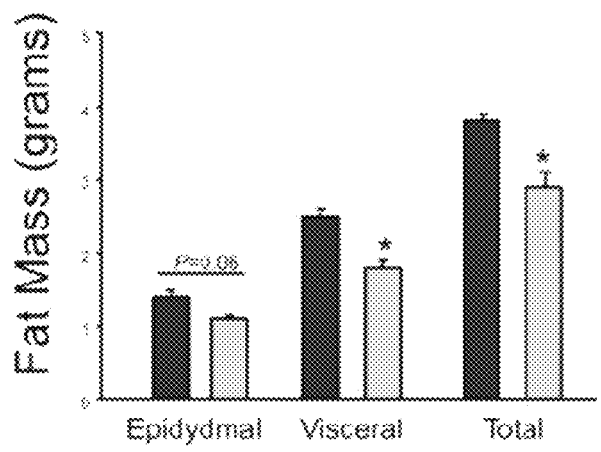
Figure 8C:
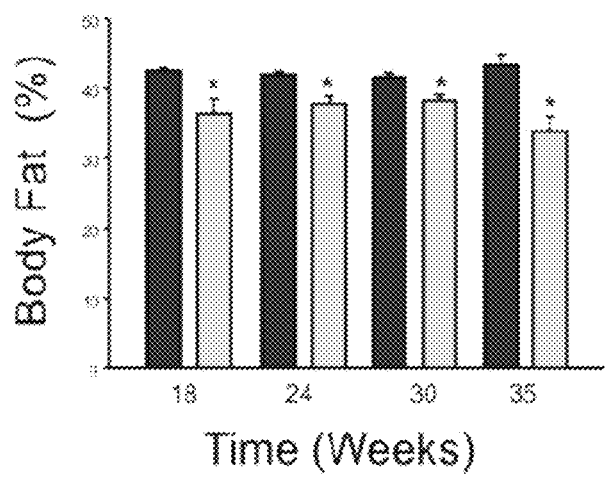
Figure 8D:
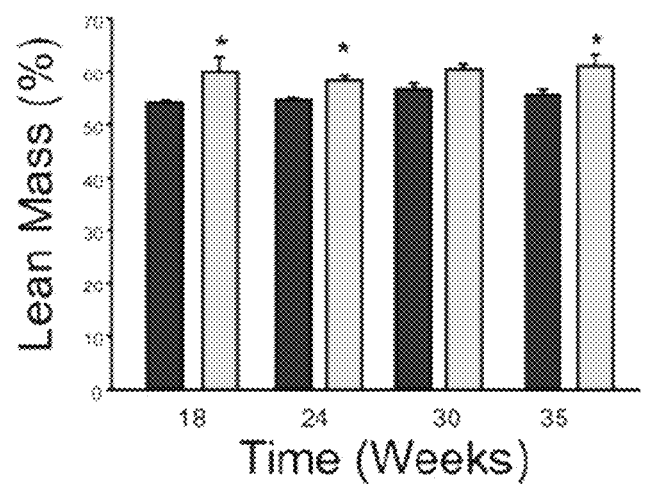
Figure 8E:
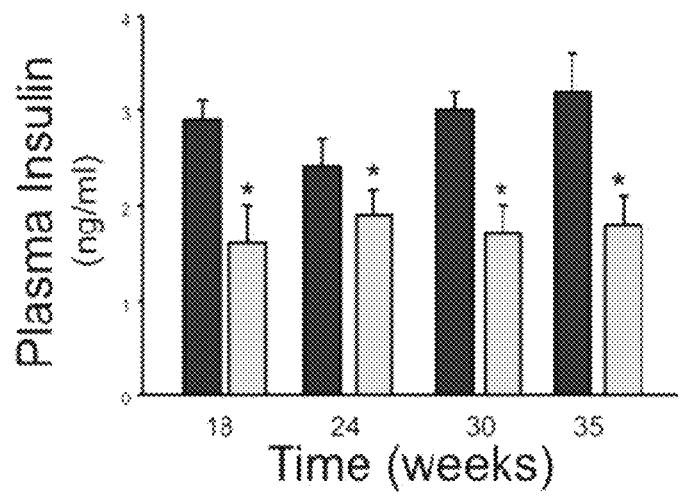
Figure 8F:
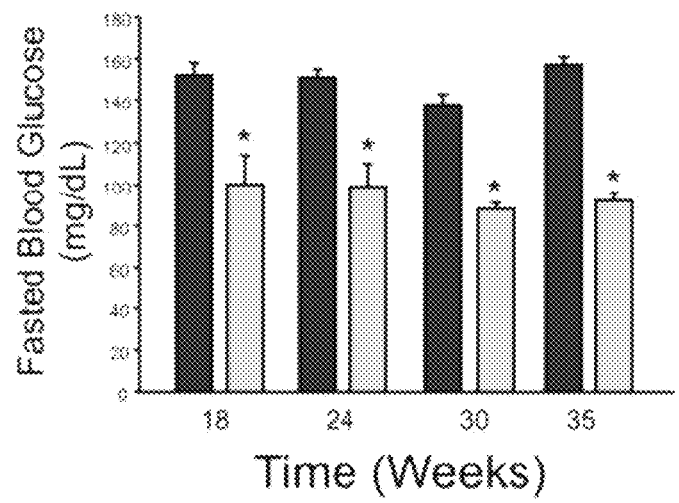

FIGS. 8A-8F: Metabolic Profile of Humanized Gilbert's Syndrome in humanized Gilbert's Syndrome (HuUGT*28) or WT (UGT1A1*1) mice. FIG. 8A shows plasma bilirubin levels. FIG. 8B shows fat mass. FIG. 8C shows body fat percentage. FIG. 8D shows lean mass. FIG. 8E shows plasma insulin levels. FIG. 8F shows blood glucose. *, P<0.05 vs WT.

Figure 9:
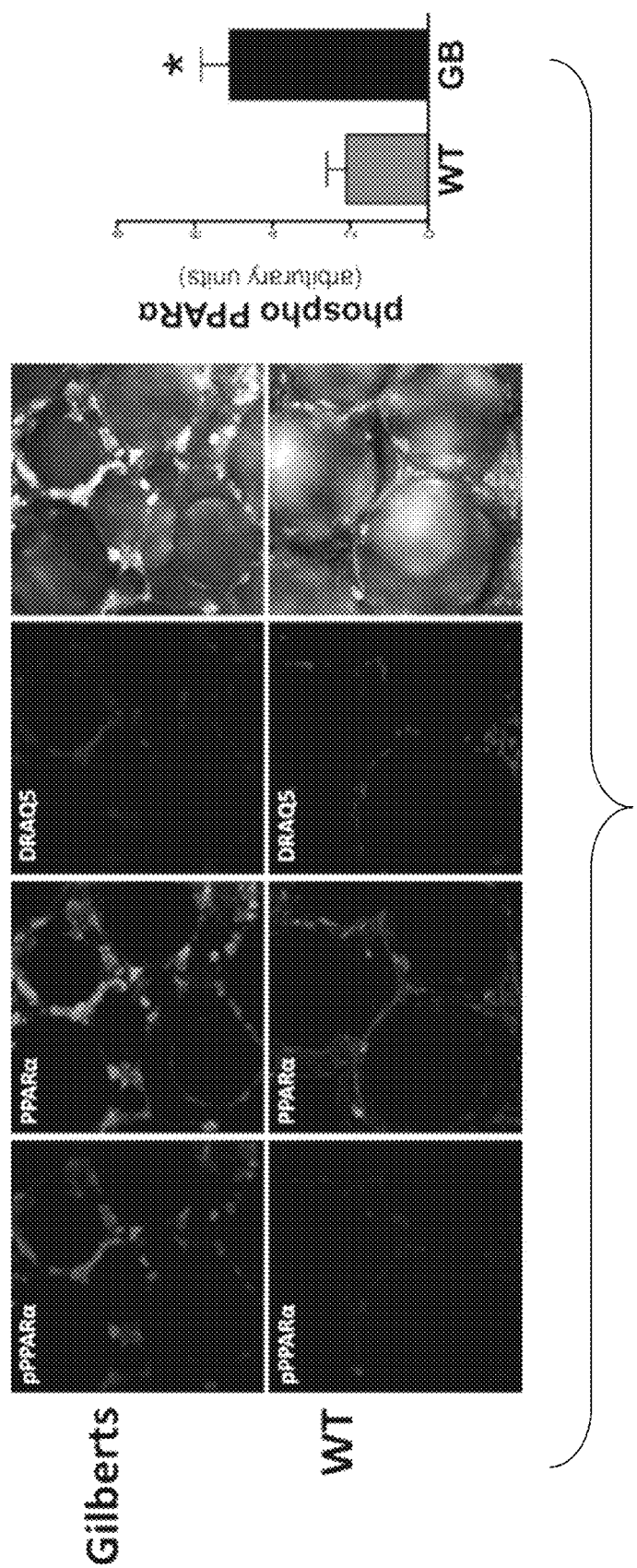

FIG. 9: Bilirubin enhances phospho PPARα in adipose tissue of Gilbert's syndrome mice (n=4).

Figure 10:
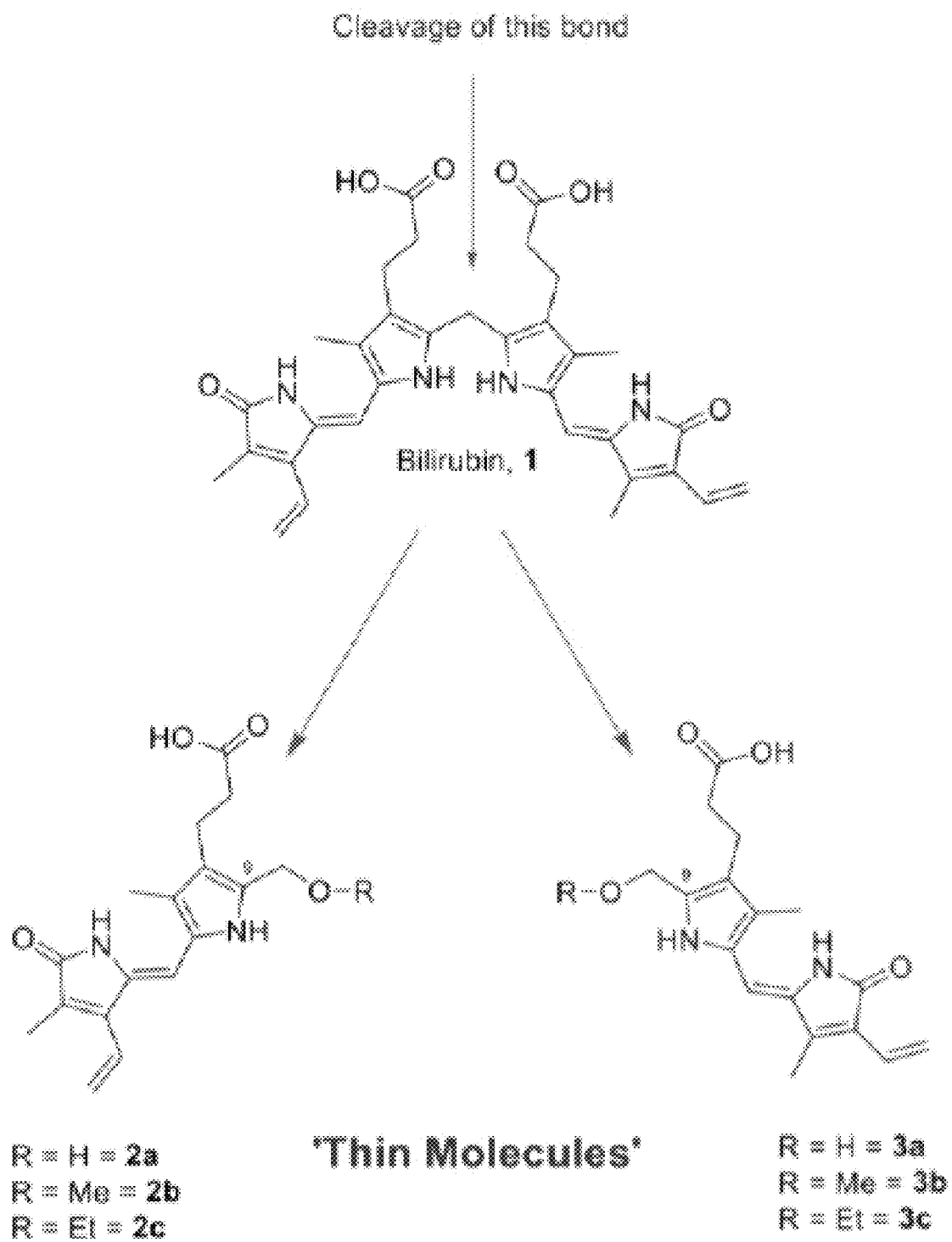

FIG. 10: A schematic diagram showing cleavage of bilirubin produces thin molecules for Formula A compounds: 2a, 2b and 2c, and for Formula B compounds: 3a, 3b and 3c.

Figure 11:
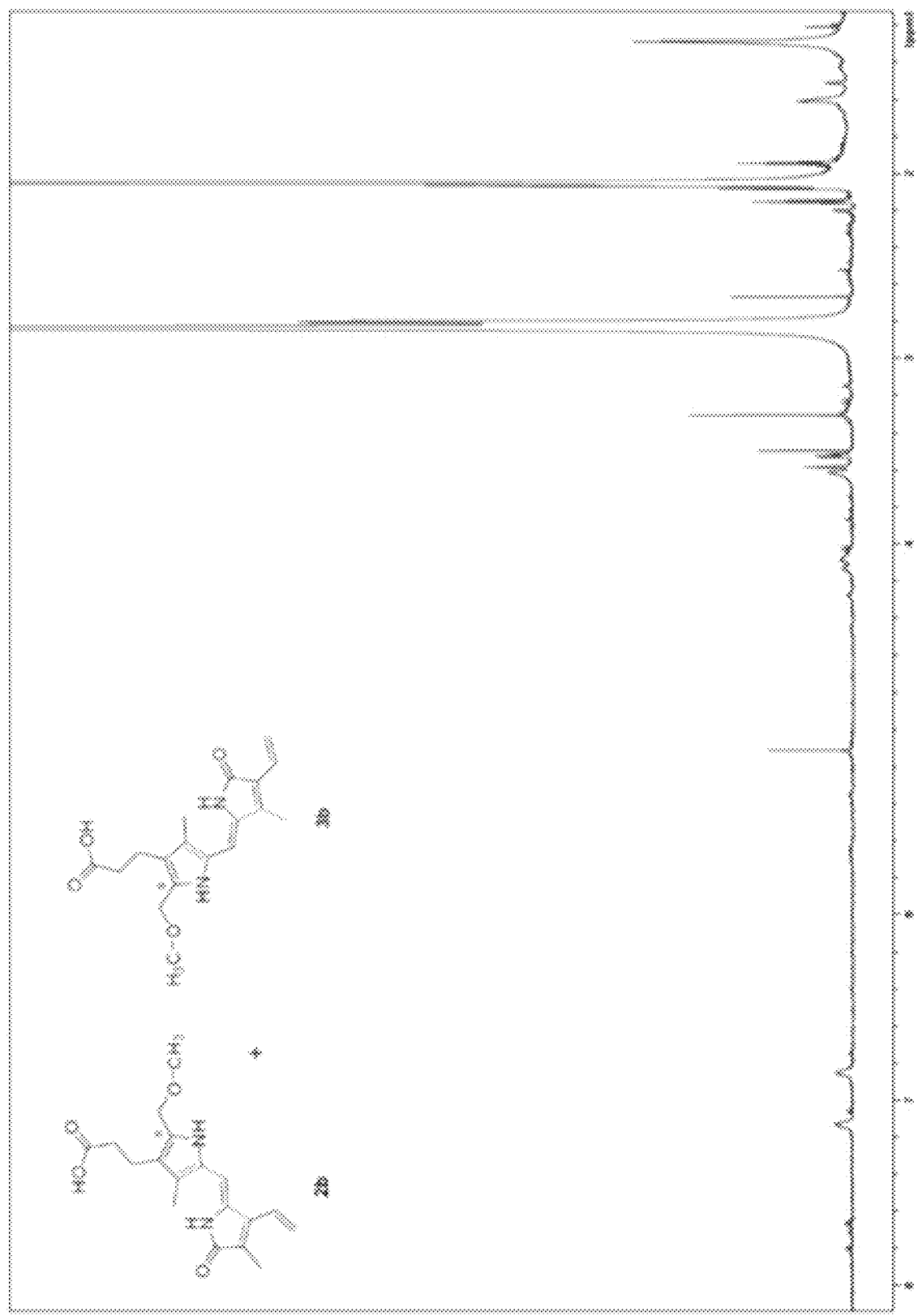

FIG. 11: $^1$H NMR of methoxy isomers 2b and 3b resulting from cleavage of 1.

Figure 12:
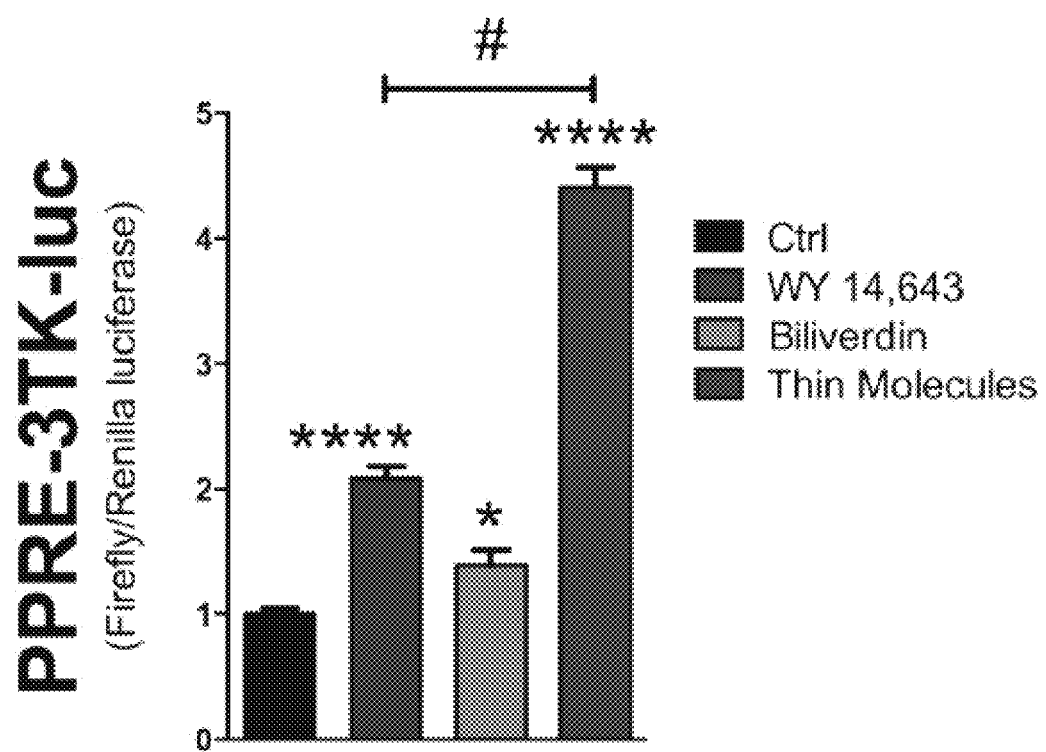

FIG. 12: Thin Molecules Activate PPARα. Cos7 cells were transfected with PPARα and RXR and treated with Ctrl (vehicle), 50 μM WY 14,643, Biliverdin, or Thin Molecules for 24 hrs. *, P<0.05 vs Ctrl; ****, P<0.0001 vs Ctrl; #, P<0.0001 vs WY.

Figure 13A:
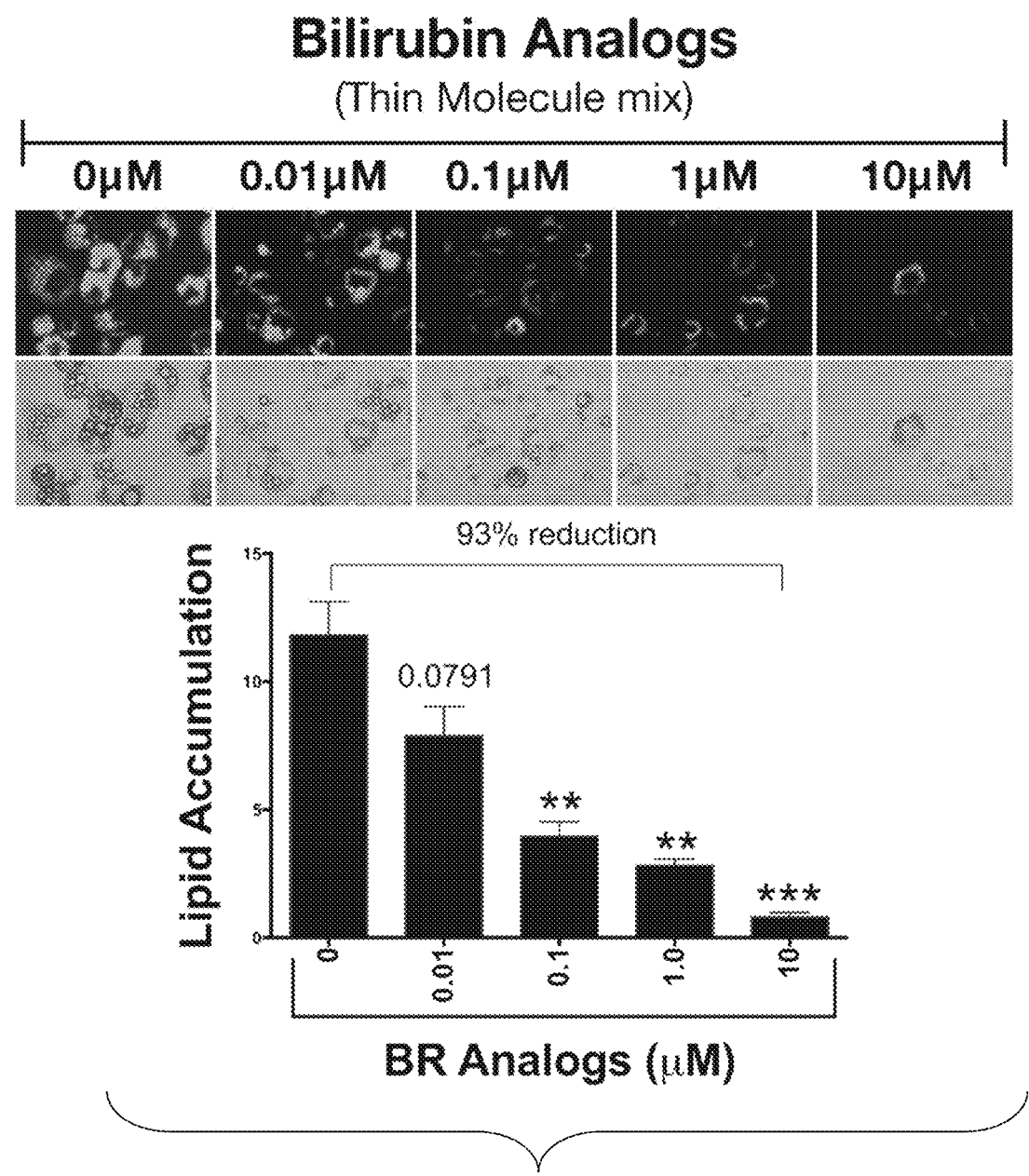
Figure 13B:
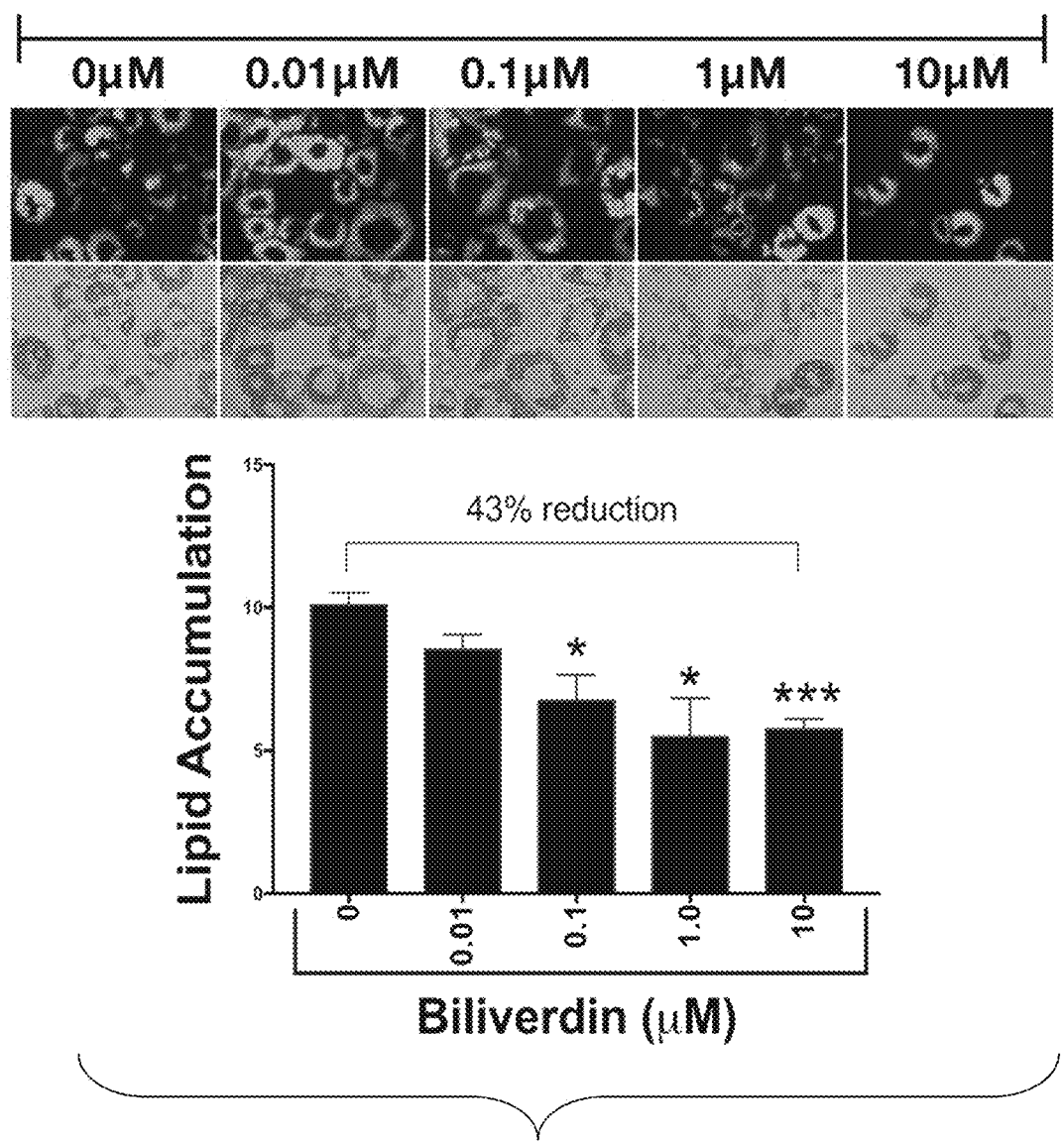

FIGS. 13A-13B: Treatment with BR analogs (Thin Molecules) during adipogenesis. BR analog treatment in 3T3-L1 adipocytes inhibited lipid accumulation. , P<0.01 vs 0 μM; *, P<0.001 vs 0 μM. n=4.

DETAILED DESCRIPTION OF THE INVENTION

Throughout this disclosure, various publications, patents, and published patent specifications are referenced by an identifying citation. The disclosures of these publications, patents, and published patent specifications are hereby incorporated by reference into the present disclosure in their entirety to more fully describe the state of the art to which this invention pertains.

It will be appreciated that any of the compounds described herein may be substituted with any number of substituents or functional moieties. In general, the term "substituted" whether preceded by the term "optionally" or not, and substituents contained in formulas, refer to the replacement of hydrogen atoms in a given structure with a specified substituent. When more than one position in any given structure may be substituted with more than one substituent selected from a specified group, the substituent may be either the same or different at every position.

It will also be appreciated by one of ordinary skill in the art that asymmetric centers may exist in any of the compounds disclosed herein. Thus, the compounds and pharmaceutical compositions thereof may be in the form of an individual enantiomer, diastereomer, or geometric isomer, or may be in the form of a mixture of stereoisomers. In certain embodiments, the compounds are enantiopure compounds. In certain other embodiments, mixtures of stereoisomers or diastereomers are provided. Additionally, the compounds encompass both (Z) and (E) double bond isomers (or cis and trans isomers) unless otherwise specifically designated. Thus, compounds generally depicted in structures herein encompass those structures in which double bonds are (Z) or (E).

The term "solvate" refers to a pharmaceutically acceptable solid form of a specified compound containing solvent molecules as part of the crystal structure. A solvate typically retains at least some of the biological effectiveness of such compound. Solvates can have different solubilities, hygroscopicities, stabilities, and other properties. Examples of solvates include, but are not limited to, compounds in combination with water, isopropanol, ethanol, methanol, DMSO, ethyl acetate, acetic acid, or ethanolamine. Solvates are sometimes termed "pseudopolymorphs."

The term "hydrate" refers to a solvate with water.

The term "racemate" refers to a mixture that contains an equal amount of enantiomers.

General Description

Provided herein are compounds producible by cleaving bilirubin at its methylene site in the center of the molecule. These compounds are referred to herein as thin molecules. The thin molecules are positional isomers, also known as regioisomers. This means that the basic carbon skeleton remains unchanged, but various groups are move around on that skeleton. In particular, the thin molecules are the positional isomers of Formula A and Formula B:

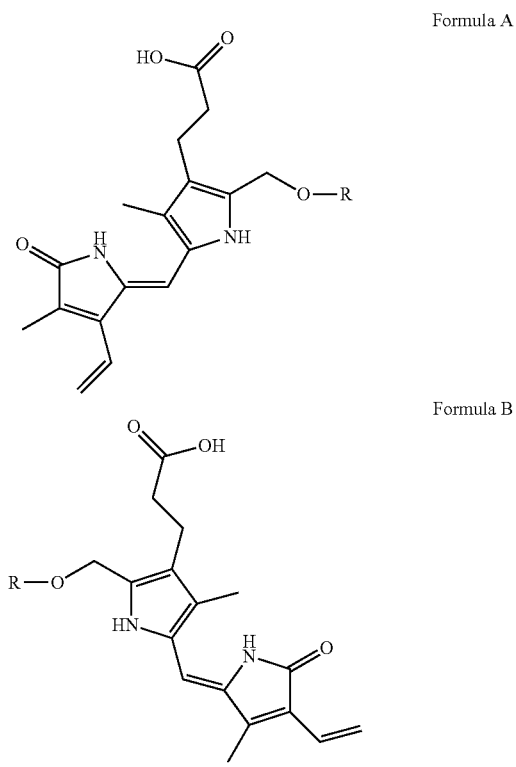

where R is either hydrogen or an alkyl group. In some embodiments, R is a substituted or unsubstituted $C_1$-$C_6$ alkyl. In some embodiments, R is methyl, ethyl, propyl, butyl, or pentyl. Non-limiting examples of thin molecules according to the present disclosure, which can be made by cleaving a bond in the center of the bilirubin structure, are shown in FIG. 10. However, it is understood that a variety of other molecules, produced by different methods, are encompassed within the present disclosure.

As the Examples herein show, bilirubin can bind directly to activate the lipid lowering nuclear receptor, peroxisome proliferator-activated receptor α (PPARα). It has been shown that increasing plasma bilirubin levels attenuates adiposity in obese mice by significantly increasing activity of PPARα. In the Examples herein, it is shown that in a humanized mouse model of Gilbert's syndrome, which have a moderate increase in plasma bilirubin levels (50%-1.5 fold elevations), the mice have reduced fat mass, increased lean mass, and lower plasma insulin and glucose levels. Without wishing to be bound by theory, it is believed that half of the bilirubin molecule mediates the binding to PPARα, which is similar in structure to known PPARα ligands. This is bolstered by molecular docking studies. (FIG. 2.) Thus, provided herein are constructed bilirubin "half molecules," referred to herein as "thin molecules." As the Examples herein show, thin molecules enhance PPARα activity higher than the known ligand WY14,643. This finding demonstrates that thin molecules, like bilirubin, binds to PPARα to decrease fat mass, which results in the prevention of type II diabetes. Thin molecules are therefore useful as a therapeutic approach for obesity and type II diabetes.

A variety of thin molecules can be produced. Luciferase constructs can be used to determine the efficacy with which the thin molecules activate PPARα. It is also believed that the thin molecules are an inhibitor of PPARγ gene regulatory activity, at least in part at genes regulating adiposity, due to the capacity of bilirubin to inhibit adipogenesis.

Thin molecules can be made by cleaving bilirubin at the methylene site in the center of the molecule, such as through a diazotization reaction followed by a nucleophilic displacement with a cosolvent. In one non-limiting example, the diazotization reaction involves reacting bilirubin with a diazotization reagent, such as sodium nitrite. In this method, the identity of the cosolvent determines the identity of the R group at the cleavage site of the resulting thin molecule. (FIG. 10.) For example, when the cosolvent is a $C_1$-$C_6$ alkanol, the resulting R is a $C_1$-$C_6$ alkyl group. In general, any method which is capable of cleaving the methylene site at the center of the bilirubin molecule can be utilized to produce thin molecules. However, other methods of making the thin molecules are encompassed within the present disclosure, including methods which do not start from bilirubin. Rather, the skilled person will recognize that the thin molecules described herein can be synthesized from other starting material through a variety of synthetic schemes. The positional isomers of Formula A and Formula B can be separated by a suitable separation method, such as various chromatography methods. As a non-limiting example, reverse-phased high-performance liquid chromatography (HPLC) can be used to separate the positional isomers. However, the positional isomers need not be separated, and can be utilized together in a mixture, for the purposes described herein.

Pharmaceutical compositions of the present disclosure comprise an effective amount of a thin molecule (an "active" compound), and/or additional agents, dissolved or dispersed in a pharmaceutically acceptable carrier. The preparation of a pharmaceutical composition that contains at least one compound or additional active ingredient will be known to those of skill in the art in light of the present disclosure, as exemplified by Remington's Pharmaceutical Sciences, 2003, incorporated herein by reference. Moreover, for animal (e.g., human) administration, it is understood that preparations should meet sterility, pyrogenicity, general safety, and purity standards as required by FDA Office of Biological Standards.

A composition disclosed herein may comprise different types of carriers depending on whether it is to be administered in solid, liquid or aerosol form, and whether it need to be sterile for such routes of administration as injection. Compositions disclosed herein can be administered intravenously, intradermally, transdermally, intrathecally, intraarterially, intraperitoneally, intranasally, intravaginally, intrarectally, intraosseously, periprosthetically, topically, intramuscularly, subcutaneously, mucosally, intraosseosly, periprosthetically, in utero, orally, topically, locally, via inhalation (e.g., aerosol inhalation), by injection, by infusion, by continuous infusion, by localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 2003, incorporated herein by reference).

The actual dosage amount of a composition disclosed herein administered to an animal or human patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a composition herein and/or additional agent is formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsules, they may be compressed into tablets, or they may be incorporated directly with the food of the diet.

In further embodiments, a composition described herein may be administered via a parenteral route. As used herein, the term "parenteral" includes routes that bypass the alimentary tract. Specifically, the pharmaceutical compositions disclosed herein may be administered, for example but not limited to, intravenously, intradermally, intramuscularly, intraarterially, intrathecally, subcutaneous, or intraperitoneally (U.S. Pat. Nos. 6,753,514, 6,613,308, 5,466,468, 5,543, 158; 5,641,515, and 5,399,363 are each specifically incorporated herein by reference in their entirety).

Solutions of the compositions disclosed herein as free bases or pharmacologically acceptable salts may be prepared in water suitably mixed with a surfactant, such as hydroxypropylcellulose. Dispersions may also be prepared in glycerol, liquid polyethylene glycols and mixtures thereof, and in oils. Under ordinary conditions of storage and use, these preparations may contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In some cases, the form must be sterile and must be fluid to the extent that easy injectability exists. It should be stable under the conditions of manufacture and storage and should be preserved against the contaminating action of microorganisms, such as bacteria and fungi. The carrier can be a solvent or dispersion medium containing, for example, water, ethanol, polyol (i.e., glycerol, propylene glycol, liquid polyethylene glycol, and the like), suitable mixtures thereof, and/or vegetable oils. Proper fluidity may be maintained, for example, by the use of a coating, such as lecithin, by the maintenance of the required particle size in the case of dispersion, and/or by the use of surfactants. The prevention of the action of microorganisms can be brought about by various antibacterial and antifungal agents, such as, but not limited to, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption such as, for example, aluminum monostearate or gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

Sterile injectable solutions are prepared by incorporating the compositions in the required amount in the appropriate solvent with various other ingredients enumerated above, as required, followed by filtered sterilization. Generally, dispersions are prepared by incorporating the various sterilized compositions into a sterile vehicle which contains the basic dispersion medium and the required other ingredients from those enumerated above. In the case of sterile powders for the preparation of sterile injectable solutions, some methods of preparation are vacuum-drying and freeze-drying techniques which yield a powder of the active ingredient plus any additional desired ingredient from a previously sterile-filtered solution thereof. A powdered composition is combined with a liquid carrier such as, but not limited to, water or a saline solution, with or without a stabilizing agent.

In other embodiments, the compositions may be formulated for administration via various miscellaneous routes, for example, topical (i.e., transdermal) administration, mucosal administration (intranasal, vaginal, etc.) and/or via inhalation.

Pharmaceutical compositions for topical administration may include the compositions formulated for a medicated application such as an ointment, paste, cream, or powder. Ointments include all oleaginous, adsorption, emulsion, and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones, and luarocapram. Possible bases for compositions for topical application include polyethylene glycol, lanolin, cold cream, and petrolatum, as well as any other suitable absorption, emulsion, or water-soluble ointment base. Topical preparations may also include emulsifiers, gelling agents, and antimicrobial preservatives as necessary to preserve the composition and provide for a homogenous mixture. Transdermal administration of the compositions may also comprise the use of a "patch." For example, the patch may supply one or more compositions at a predetermined rate and in a continuous manner over a fixed period of time.

In certain embodiments, the compositions may be delivered by eye drops, intranasal sprays, inhalation, and/or other aerosol delivery vehicles. Methods for delivering compositions directly to the lungs via nasal aerosol sprays has been described in U.S. Pat. Nos. 5,756,353 and 5,804,212 (each specifically incorporated herein by reference in their entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts and could be employed to deliver the compositions described herein. Likewise, transmucosal drug delivery in the form of a polytetrafluoroethylene support matrix is described in U.S. Pat. No. 5,780,045 (specifically incorporated herein by reference in its entirety), and could be employed to deliver the compositions described herein.

It is further envisioned the compositions disclosed herein may be delivered via an aerosol. The term aerosol refers to a colloidal system of finely divided solid or liquid particles dispersed in a liquefied or pressurized gas propellant. The typical aerosol for inhalation consists of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight, and the severity and response of the symptoms.

In particular embodiments, the compounds and compositions described herein are useful for treating, preventing, or ameliorating obesity and type II diabetes. Furthermore, the compounds and compositions herein can be used in combination therapies. That is, the compounds and compositions can be administered concurrently with, prior to, or subsequent to one or more other desired therapeutic or medical procedures or drugs. The particular combination of therapies and procedures in the combination regimen will take into account compatibility of the therapies and/or procedures and the desired therapeutic effect to be achieved. Combination therapies include sequential, simultaneous, and separate administration of the active compound in a way that the therapeutic effects of the first administered procedure or drug is not entirely disappeared when the subsequent procedure or drug is administered.

It is further envisioned that the compounds and methods described herein can be embodied in the form of a kit or kits. A non-limiting example of such a kit is a kit for making a thin molecule, the kit comprising bilirubin and a diazotization reagent in separate containers, where the containers may or may not be present in a combined configuration. Many other kits are possible, such as kits further comprising a cosolvent, or further comprising a pharmaceutically acceptable carrier, diluent, or excipient. The kits may further include instructions for using the components of the kit to practice the subject methods. The instructions for practicing the subject methods are generally recorded on a suitable recording medium. For example, the instructions may be present in the kits as a package insert or in the labeling of the container of the kit or components thereof. In other embodiments, the instructions are present as an electronic storage data file present on a suitable computer readable storage medium, such as a flash drive, CD-ROM, or diskette. In other embodiments, the actual instructions are not present in the kit, but means for obtaining the instructions from a remote source, such as via the internet, are provided. An example of this embodiment is a kit that includes a web address where the instructions can be viewed and/or from which the instructions can be downloaded. As with the instructions, this means for obtaining the instructions is recorded on a suitable substrate.

Further provided is a method of determining coverage of health insurance reimbursement or payments, the method comprising denying coverage or reimbursement for a treatment, wherein the treatment comprises a thin molecule.

EXAMPLES

Example I—Bilirubin is a Ligand for PPARα

Bilirubin was found to have the function as a ligand for PPARα. It is shown in this Example that bilirubin can bind directly to PPARα and increase transcriptional activity. Biliverdin, the precursor of bilirubin, comparison of known PPARα ligands, WY 14,643 and fenofibrate, on PPARα activation showed that fenofibrate and biliverdin have similar activation properties. Treatment of 3T3-L1 adipocytes with biliverdin suppressed lipid accumulation and upregulated PPARα target genes. Wild-type and PPARα KO mice on a high fat diet were treated with fenofibrate or bilirubin for seven days, and it was found that both fenofibrate and bilirubin signal through PPARα-dependent mechanisms. Furthermore, the effect of bilirubin on lowering glucose and reducing body fat percentage was blunted in PPARα KO mice. These results demonstrate the function of bilirubin as an agonist of PPARα, which mediates the protection from adiposity afforded by moderate increases in bilirubin.

Bilirubin directly binds to activate PPARα, which increases target genes to reduce adiposity. The ability of bilirubin to act as an activator of nuclear hormone receptors such as PPARα may explain the beneficial effects of moderate increases in plasma bilirubin levels that have been observed in patients with GS.

Materials and Methods

Animals

With respect to animals, the procedures and protocols conform to the National Institutes of Health Guide for the Care and Use of Laboratory Animals, and were approved by the Institutional Animal Care and Use Committee of the University of Mississippi Medical Center. Tests were performed on 16 week old male PPARα knockout and wild-type mice on a C57 genetic background purchased from Jackson Labs (Bar Harbor, Me.). Mice were housed under standard conditions and allowed full access to a control 17% fat diet (Teklad 22/5 rodent diet, #860, Harland Laboratories, Inc., Indianapolis, Ind.) for 4 weeks. After this time, mice were switched to a 60% high fat diet (diet # D12492, Research Diets, Inc., New Brunswick, N.J.) for an additional 6 weeks. Mice were treated with either bilirubin (30 mg/kg, i.p.) or fenofibrate (90 mg/kg, i.p.) every 48 hours over the last week of the high fat diet. Control mice were not treated. Mice were euthanized on the last day of the test, at which time all organs were collected and weighed. Bilirubin was prepared in 0.1 M NaOH (pH 7.7) and fenofibrate was prepared in corn oil.

Body Composition (EchoMRI)

Body composition changes were assessed at the end of the test using magnetic resonance imaging (EchoMRI-900™, Echo Medical System, Houston, Tex.). MRI measurements were performed on conscious mice placed in a thin-walled plastic cylinder with a cylindrical plastic insert added to limit movement of the mice. Mice were briefly submitted to a low intensity electromagnetic field and fat mass, lean mass, free water, and total water were measured.

Fasting Glucose and Insulin

Following an 8 hour fast, a blood sample was obtained via orbital sinus under isoflurane anesthesia. Blood glucose was measured using an Accu-Chek® Advantage glucometer (Roche, Mannheim, Germany). Fasting plasma insulin concentrations were determined by ELISAs (Linco Insulin ELISA kit).

Measurement of Plasma Bilirubin, Alanine Aminotransferase (ALT), and Aspartate Aminotransferase (AST)

Total bilirubin was measured from 20 μL of plasma using the Total Bilirubin IR700® Assay Kit (Synermed, Westfield, Ind.) according to the manufacturer instructions. The bilirubin assay was calibrated with a standard curve derived from a bilirubin solution provided by the manufacturer. Total bilirubin was determined by measurement at 700 nm on a plate reader. Plasma samples from individual mice were measured in duplicate and then averaged. The concentrations are expressed as mg/dL Plasma alanine aminotransferase (ALT) and aspartate aminotransferase (AST) levels were determined in 50 μL of plasma by colorimetric assay (Cobas, Rochce Diagnostics, Indianapolis, Ind.). Assays were performed according to the manufacturer's guidelines and samples were read on a Roche Cobas c501 analyzer. The concentrations were expressed as units/L.

Measurement of Plasma FGF21

Plasma levels of FGF21 were measured from 50 μL of plasma using a specific mouse/rat FGF21 ELISA (Quantikine® ELISA, R & D Systems, Minneapolis, Minn.)

according to the manufacturer's instructions. The FGF-21 ELISA was calibrated with a standard curve derived from a mouse/rat FGF21 standard provided by the manufacturer. FGF21 levels were measured in duplicate from individual mice and FGF21 levels were determined by measurement at 450 nm on a plate reader. The concentrations are expressed as ng/mL.

Cell Lines and Culture

The mouse 3T3-L1 preadipocyte, Hepa1c1c7, and Cos7 green kidney monkey cells were routinely cultured and maintained in Dulbecco's Modified Eagles's Medium (DMEM) containing 10% bovine calf serum or FBS with 1% penicillin-streptomycin. The vector and PPARα 3T3-L1 cell lines were grown as previously described.

Promoter Reporter Assays

An expression vector for PPARα-pcDNA3.1+ was constructed as previously described. A PPARα minimal promoter PPRE-3tk-luc activity was measured by luciferase, and pRL-CMV Renilla reporter for normalization to transfection efficiency. Transient transfection was achieved using GeneFect® (Alkali Scientific, Inc.). Twenty-four-hour post-transfected cells were lysed and the luciferase assay was performed using the Promega® dual luciferase assay system (Promega, Madison, Wis.).

In Silico Molecular Modeling and Docking Analysis of Bilirubin

Docking studies were carried out using Tripos's Surflex-dock® suite on SYBYL-X® molecular modeling package. Briefly, PPARα x-ray crystal structure was imported from RCSB Protein Data Bank (PDB ID: 2P54). The protein structure was prepared using SYBYL's Biopolymer tool where terminal groups were appropriately functionalized, and the acidic residues were maintained at the physiological protonated state. The standard AMBER and MMFF94 charges were assigned to the bio-molecule and the small molecules, respectively. The docking model was internally validated where the 'crystal structure bound ligand' was the first energy minimized using default setting followed by docking on the receptor site using the dock model. The top scoring conformation of ligand was aligned with the 'bound crystal structure of the ligand.' The two conformations—the docked model conformation and the crystal conformation—were aligned one-over-the-other. Similarly, the bilirubin chemical structure was sketched and energy minimized prior to docking into the receptor site.

EAH Sepharose™ 4B Coupled to Bilirubin, Biliverdin, or WY 14,643

The ligand coupling was performed according to the GE Healthcare instructions (71-7097-00 AE, pg. 6) for EAH Sepharose™ 4B. The procedure in the online instructions was titled "A general ligand coupling procedure". In summary, concentrations of ligands (bilirubin, biliverdin, or WY 14,643) were 5 times the molar excess calculated for the free amine groups (12 μmol/mL drained matrix). Resin coupling procedures were conducted in a DMF/$H_2O$ solvent system (1:1) with a final concentration of 0.1 M EDC*HCl. Suspensions were rotated end-over-end for 24-36 h at room temperature (however, see note below regarding bilirubin solubility). Upon completion, resins were washed according to the GE instructions (3 alternating washings with 0.5 M NaCl containing 0.1 M sodium acetate pH 4.5 and 0.5 M NaCl containing 0.1 M Tris pH 8) over a 10-15 μm fritted filter. As an additional step to the GE instructions, matrix-coupled bilirubin and biliverdin coupled preparations were further washed with 50% DMSO/$H_2O$ solutions (250 mL) to remove any unreacted ligand. The filtrate was nearly colorless after this step. For WY 14,643, 50% DMF/$H_2O$ solutions (100 mL) were used to wash off any unreacted ligand. The resins were suspended in 20% EtOH/$H_2O$ (15 mL) and stored at 4° C. for 16 h in capped sample vials. The ligand-coupled resin settles overnight and the supernatant was carefully decanted until minimal amounts of 20% EtOH/$H_2O$ covered the resin. Aliquots (~1.5 mL) from each sample were suspended in the presence and absence of 1 M acetic acid, which blocks unreacted free amines on the resin that did not react. Aliquots for samples designated "+AA" were subjected to 1 M acetic acid overnight, while "-AA" describes no acetic acid treatment and simply suspended in 20% EtOH/$H_2O$. In the case for +AA samples, after 16 h, the acetic acid solution was carefully decanted and then re-suspended in the storage solution (20% EtOH/$H_2O$). When comparing the results of resin preparations in the presence and absence of AA, it was determined that the AA treatment had no effect on bilirubin binding PPARα. However, the AA treatment attenuated WY 14,643 binding PPARα. All samples were stored in 20% EtOH/$H_2O$ before use.

Due to the limited solubility of bilirubin in most organic solvents, preparations of resins in which bilirubin solutions were either heated (75° C. for 90 min) or not heated in DMF/$H_2O$ prior to addition of EDC*HCl were compared. This was to help increase the solubility of bilirubin in solution. Ethylene glycol, an ideal solvent, was not an appropriate co-solvent due to bilirubin's limited solubility. The decrease in PPARα binding in resin preparations where bilirubin was heated indicates bilirubin is less stable with heating. Ultimately, as demonstrated by the data in FIGS. 3A-3C, a sufficient concentration of bilirubin was achieved at room temperature. Both biliverdin and WY 14,643 were readily soluble in organic solvents, and application of heat was not attempted. Bilirubin was purchased commercially from Frontier Scientific. Biliverdin and WY 14,643 were purchased from Sigma-Aldrich.

Whole Cell Extraction

Cells were washed and collected in IX PBS followed by centrifugation at 1500×g for 10 min. The supernatant was discarded and the pellet was re-suspended in IX PBS. After a short spin at 20,800×g for 5 min at 4° C. the pellet was rapidly frozen on dry ice ethanol mix and stored at −80° C. for 30 min. The frozen pellet was then re-suspended in 3 volumes of cold whole cell extract buffer (20 mM HEPES, 25% glycerol, 0.42M NaCl, 0.2 mM EDTA, pH 7.4) with protease inhibitors and incubated on ice for 10 min. The samples were centrifuged at 100,000×g for 5 min at 4° C. Protein levels were measured spectrophotometrically by a Nanodrop 2000® (Thermo Fisher Scientific, Wilmington, Del.). The supernatants were either stored at −80° C. or used immediately for Western analysis to determine protein expression levels.

Quantitative Real-Time PCR Analysis

Total RNA was extracted from mouse tissues using 5-Prime PerfectPure® RNA Cell Kit (Fisher Scientific Company, LLC). Total RNA was read on a NanoDrop 2000® spectrophotometer (Thermo Fisher Scientific, Wilmington, Del.), and cDNA was synthesized using High Capacity cDNA Reverse Transcription Kit (Applied Biosystems). PCR amplification of the cDNA was performed by quantitative real-time PCR using TrueAmp® SYBR Green qPCR SuperMix (Advance Bioscience). The thermocycling protocol consisted of 10 min at 95° C., 40 cycles of 15 sec at 95° C., 30 sec at 60° C., and 20 sec at 72° C., and finished with a melting curve ranging from 60-95° C. to allow distinction of specific products. Normalization was performed in separate reactions with primers to GAPDH.

Generation of Lentiviral Constructs

To establish a 3T3-L1 or Hepa1c1c7 cell line that have PPARα stably overexpressed, mouse PPARα cDNA was ligated into the NotI/BamHI sites of the pQXCIP vector and transformed in DH5α cells (Invitrogen, Carlsbad, Calif.). The construct was co-transfected together with vectors expressing gag-pol, REV, and VSV-G into 293FT cells (Invitrogen) to generate a third generation lentiviral construct. Transfection was achieved using GeneFect® (Alkali Scientific, Inc.) using 100 ng total DNA per cm$^2$ of the growth plate or well. The supernatants were harvested, and the cell debris was removed by centrifugation at 2000×g. The supernatant was used to infect 3T3-L1 or Hepa1c1c7 cells after addition of polybrene (5 ng/ml, Sigma Chemical Co., St. Louis, Mo.) to establish cell lines with stable overexpression of a PPARα overexpressing (3T3-PPARα) or expressing empty vector (3T3-Vector). After 72 h the cells were selected with puromycin, and positive cells were confirmed by Western blotting and used for experiments.

Adipogenesis Assay

Adipogenic differentiation of 3T3-L1 cells was achieved by treatment with 1 μM Dex, 830 nM insulin, and 100 μM isobutylmethylxanthine in 10% FBS until Day 9. Upon differentiation, cells were stained with Nile Red to visualize lipid content, and densitometry was used as a direct measure. Total RNA extracted from Nile Red stained cells was used for real time PCR analysis.

Gel Electrophoresis and Western Blotting

Whole cell extracts (WCE) were prepared by freezing the cell pellet overnight at −80° C. The pellet was then resuspended in 3 volumes of WCE buffer (20 mM HEPES, 0.42 M NaCl, 0.2 M EDTA, 25% glycerol, pH 7.4) plus protease inhibitor cocktail and incubated on ice for ten min followed by 100,000×g centrifugation at 4° C. Protein samples were resolved by SDS polyacrylamide gel electrophoresis and electrophoretically transferred to Immobilon-FL membranes. Membranes were blocked at room temperature for 1 hour in TBS [TBS; 10 mM Tris-HCl (pH 7.4) and 150 mM NaCl] containing 3% BSA. Subsequently, the membrane was incubated overnight at 4° C. with PPARα or HSP90 antibodies (Santa Cruz Biotechnology, Dallas, Tex.). After three washes in TBST (TBS plus 0.1% Tween 20), the membrane was incubated with an infrared anti-rabbit (IRDye 800®, green) or anti-mouse (IRDye 680®, red) secondary antibody labeled with IRDye® infrared dye (LI-COR Biosciences) (1:15,000 dilution in TBS) for 2 hours at 4° C. Immunoreactivity was visualized and quantified by infrared scanning in the Odyssey system (LI-COR Biosciences).

Statistical Analysis

Data were analyzed with Prism 6 (GraphPad® Software, San Diego, Calif.) using analysis of variance combined with Tukey's post-test to compare pairs of group means or unpaired t tests. Results are expressed as mean±SEM. Additionally, one-way ANOVA with a least significant difference post hoc test was used to compare mean values between multiple groups, and a two-tailed, and a two-way ANOVA was utilized in multiple comparisons, followed by the Bonferroni post hoc analysis to identify interactions. p values of 0.05 or smaller were considered statistically significant.

Results and Discussion

Bilirubin plasma levels have been shown to be inversely correlated with lipid and glucose, and increasing levels have been shown to be beneficial for obesity, type II diabetes, and cardiovascular disease. It has also been shown that cobalt protoporphyrin (CoPP) treated mice had higher levels of bilirubin, and increased PPARα expression. Whether bilirubin directly binds to the activated nuclear receptor was investigated.

Figure 1A:
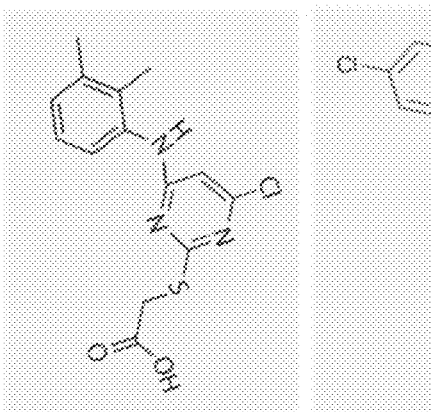
FIGS. 1A-1B: Structural comparison of PPARα ligands.
Figure 1A:
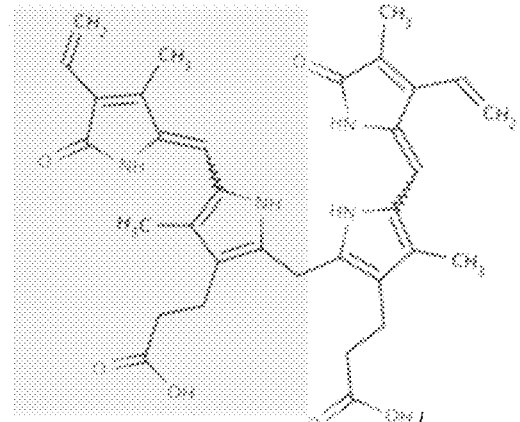
Figure 1B:
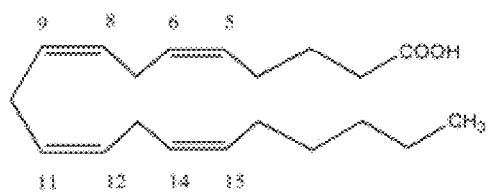
Figure 1B:
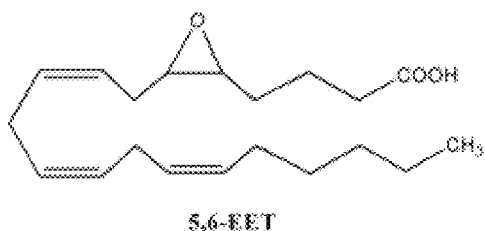
Figure 1B:
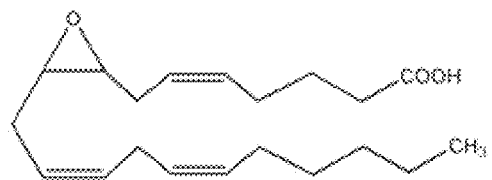
Figure 1B:
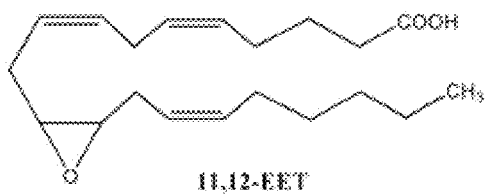
Figure 1B:
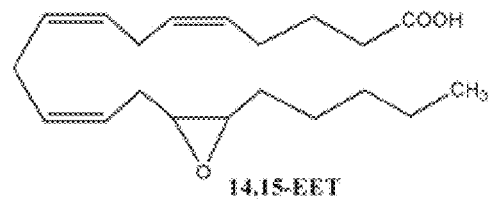
Figure 2A:
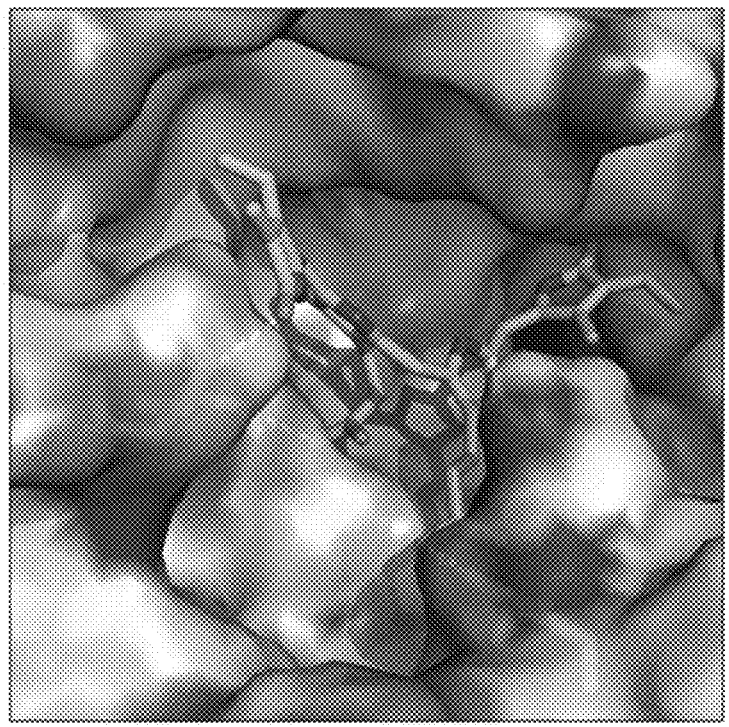
FIGS. 2A-2B: Docking models showing that bilirubin binds to the ligand-binding pocket of PPARα.
Figure 2B:
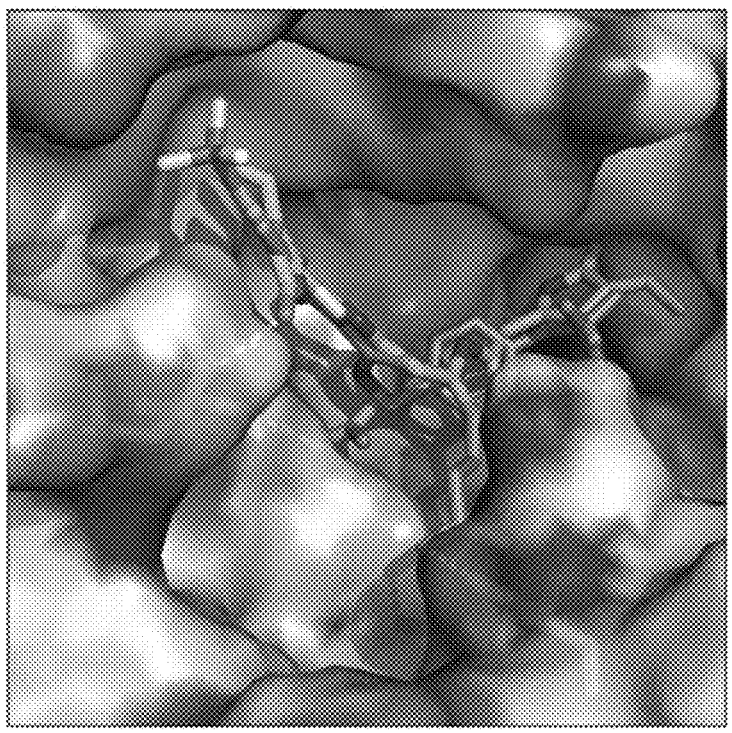

A number of synthetic drugs have been developed as PPARα agonists, including WY 14,643 and fibrates that are used to treat hyperlipidemia. Upon comparison of WY 14,643 and fenofibrate, PPARα ligands have structural similarities to bilirubin (FIG. 1), making bilirubin a ligand that could activate the low fidelity ligand-binding pocket of PPARα. There have been numerous endogenous ligands also identified for PPARα that includes several unsaturated fatty acids and their derivatives such as epoxyeicosatrienoic acids (EETs). PPARα has been shown to have anti-tumorigenic properties that are mediated by arachidonic acid epoxygenase. The CYP2C and CYP2J epoxygenases metabolize arachidonic acid to 5,6-, 8,9-, 11,12-, and 14, 15-EETs (FIG. 1B), which have been shown to bind and activate PPARα induced gene activity. However, the structures of the synthetic and endogenous PPARα ligands are diverse. An in silico modeling/docking analysis shows that bilirubin docks well into the ligand-binding pocket of PPARα (FIG. 2A). In fact, bilirubin binds to the same site occupied by the known PPARα ligand GW735 (FIG. 2B). A comparison of the two structures, the docked model conformation and the crystal structure of GW735, showed that they aligned one-over-the-other, indicating tight binding in the docking model. Also, bilirubin exploits some additional interaction with receptor residues such as the H-bonding interaction between Threonine 223 and the carboxylate group of bilirubin, indicating a stronger binding. Furthermore, bilirubin engages with the receptor through a thermodynamically more stable 'twist' conformation. The receptor sites appear to have two relatively distinct binding pockets, a more lipophilic left zone and more hydrophilic region on the right, which may cause the ligands to 'arch' and engage with the two sites.

Figure 3A:
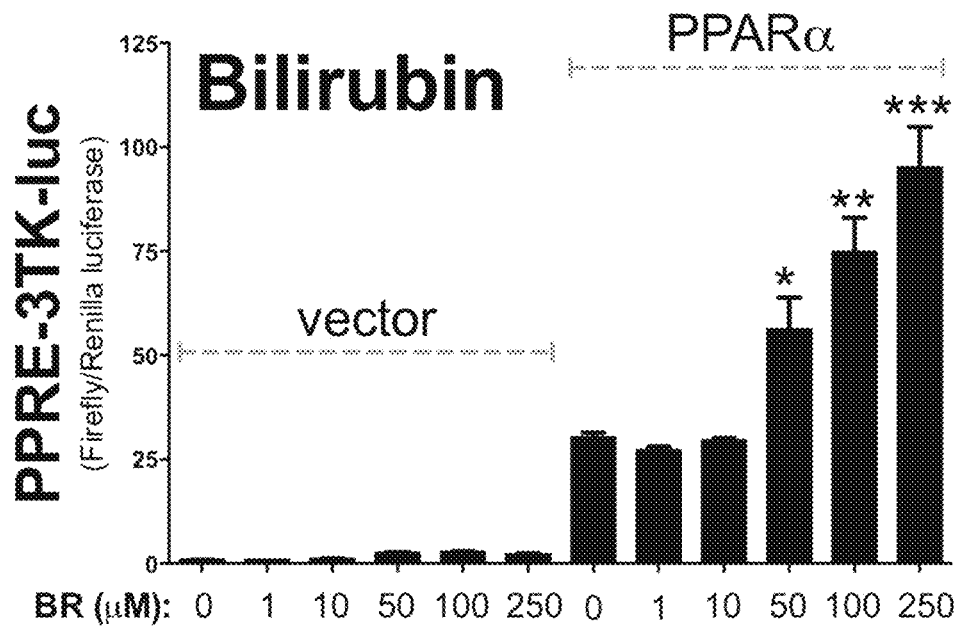
FIGS. 3A-3C: Results of a PPARα activity assay showing that bilirubin and biliverdin activate PPARα activity. Cos7 cells were transiently transfected with a minimal PPARα responsive promoter luciferase construct (PPRE-3tk-luc) for 24 hours along with an empty vector and a vector containing PPARα cDNA (overexpression). The cells were treated for 24 hours with a dose dependent increase of bilirubin (FIG. 3A) or biliverdin (FIG. 3B) to determine PPARα activity. *, $P<0.001$; , $P<0.01$; *, $P<0.05$ (vs. 0 μM PPARα); (±S.E.; n=4). To compare biliverdin (BV), WY 14,643 (WY), and fenofibrate (Feno) on PPARα activity, the minimal promoter PPRE-3tk-luc luciferase construct was used and treated for 24 hours with PPARα overexpressed and then treated with 50 μM each for 24 hours.
Figure 3B:
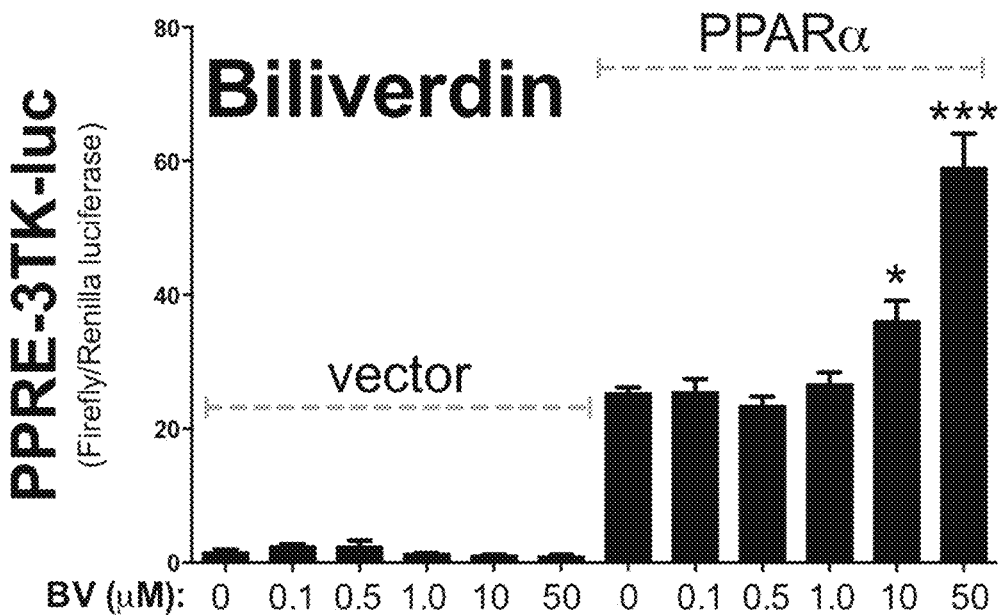
Figure 3C:
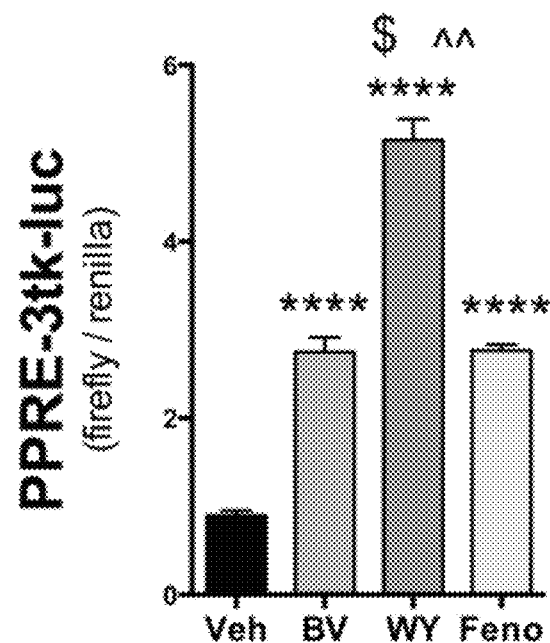

To determine if bilirubin or its precursor, biliverdin, can activate PPARα, a dose dependence of each molecule was performed in the presence and absence of PPARα (FIGS. 3A-3B). In the absence of PPARα, biliverdin or bilirubin did not activate the PPRE-3tk-luc promoter. A dose dependence treatment showed that biliverdin and bilirubin significantly (p<0.05) increased PPARα activity. To compare biliverdin/bilirubin to known PPARα agonists, WY 14,643 and fenofibrate, the minimal PPRE-3tk-luc promoter was used to determine the level of activation among the ligands. Biliverdin, Wyo. 14,643, and fenofibrate all significantly (p<0.0001) increased PPARα activity at the minimal luciferase promoter (FIG. 3C). WY 14,643 significantly (p<0.001) increased promoter activity of PPRE-3tk-luc higher than biliverdin or fenofibrate. Interestingly, biliverdin and fenofibrate had the same level of PPARα activation.

Figure 4A:
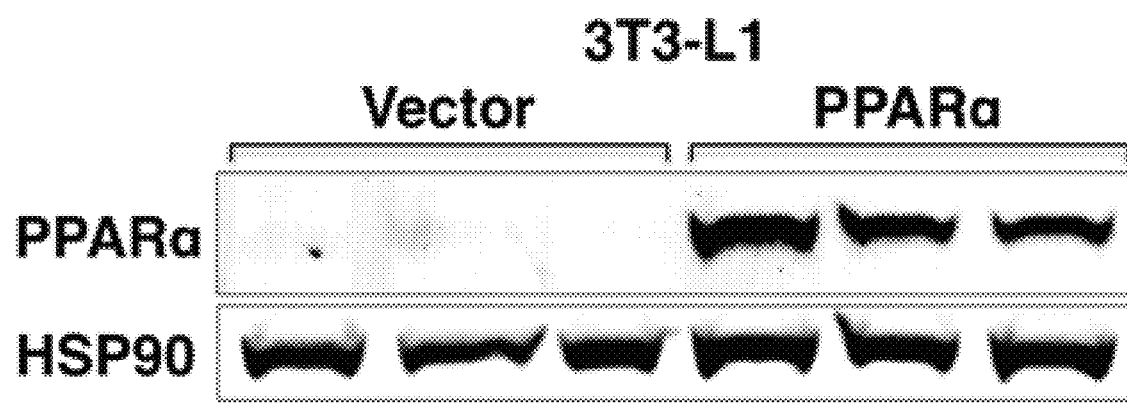
FIGS. 4A-4E: Bilirubin binds directly to PPARα to increase endogenous gene activity.
Figure 4B:
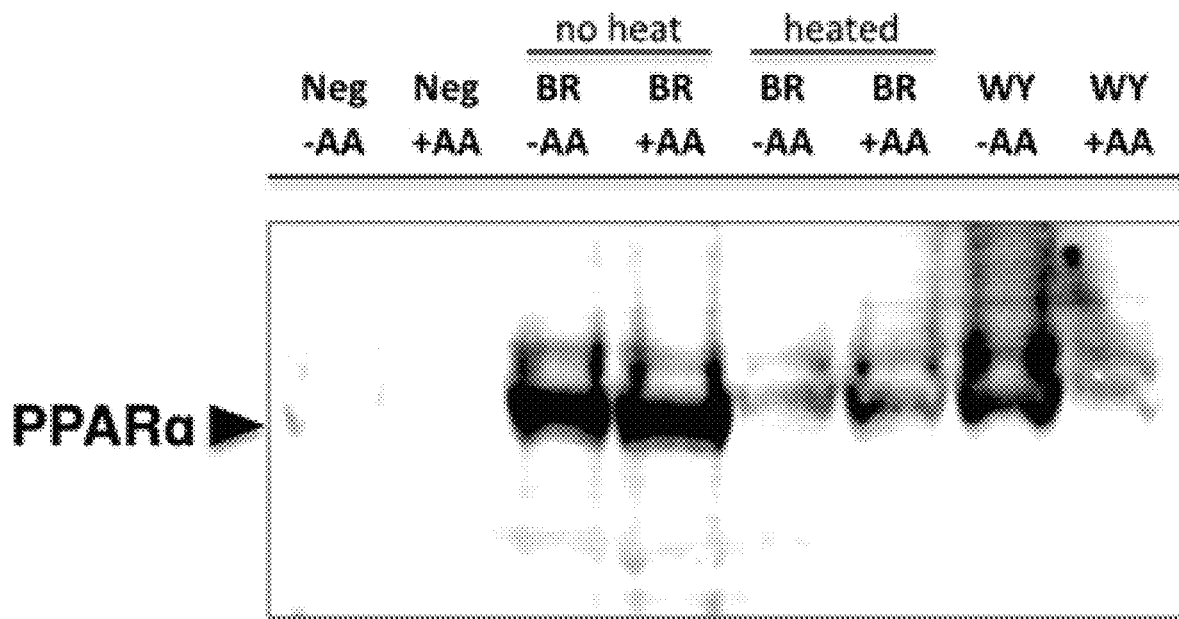
Figure 4C:
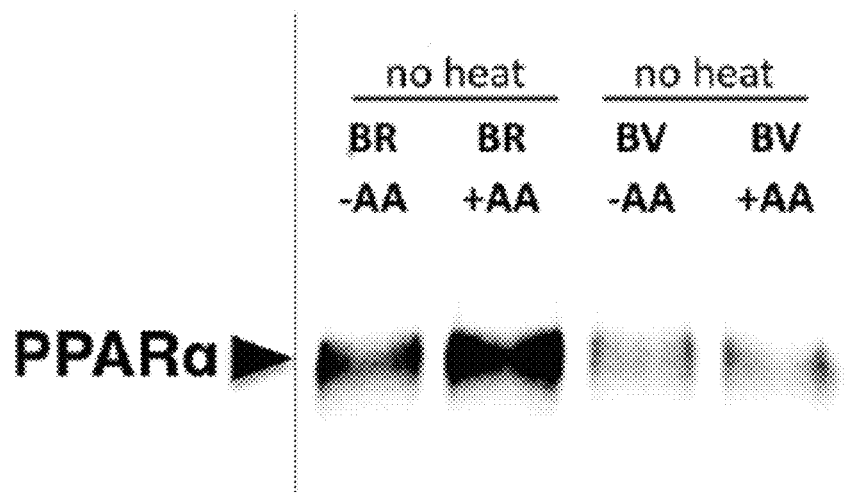

To show that bilirubin/biliverdin can bind PPARα as well as regulate endogenous genes, a stable cell line was constructed via lentivirus with PPARα cDNA overexpressed (PPARα OE) or vector control in 3T3-L1 cells (FIG. 4A), as they have been shown to have low to no PPARα expression in the undifferentiated state. First, to determine if bilirubin is directly binding to activate PPARα, the carboxylic acid group of either WY 14,643 or bilirubin was coupled to amino-functionalized sepharose beads (described in detail in the Materials and Methods above). PPARα OE 3T3-L1 cells were used to perform pull-down assays to determine that PPARα directly binds bilirubin and WY 14,643 (FIG. 4B). The pull-down results show that PPARα can directly bind to bilirubin and the known PPARα agonist WY 14,643. To compare the binding of biliverdin and bilirubin to PPARα, PPARα OE 3T3-L1 cells were used for a pull-down assay with sepharose beads cross-linked with either bilirubin or biliverdin. Interestingly, bilirubin had preferential binding to PPARα compared to biliverdin (FIG. 4C). The double bond linking the two dipyrrin-1-one functionalities of biliverdin may cause a rigidity not seen in bilirubin (where the two dipyrrin-1-one groups are linked by a saturated methylene group) and may not allow the bending/twisting in the conformation (seen FIG. 2A). The thermodynamic stability of bilirubin as compared to structurally fixed biliverdin in the PPARα binding pocket may explain the difference in binding. Ultimately, these results indicate that biliverdin must be reduced to bilirubin intracellularly through the enzyme biliverdin reductase (BVR), to effect PPARα activity.

Figure 4D:
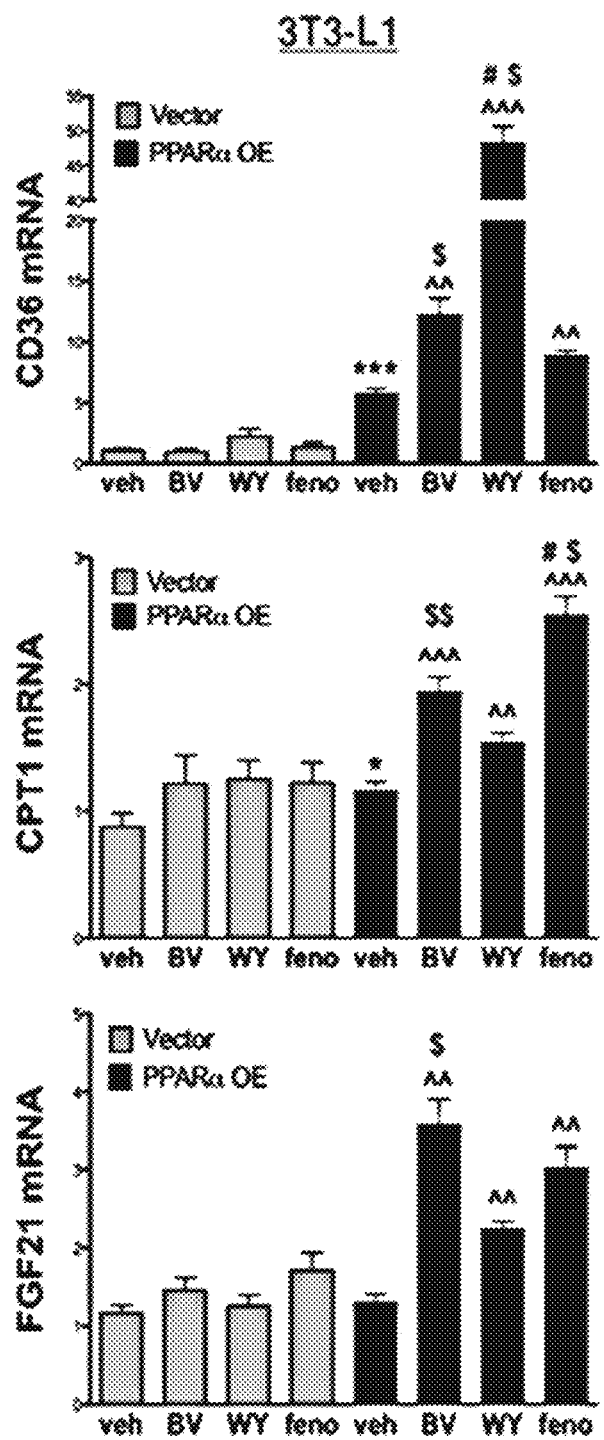
Figure 4E:
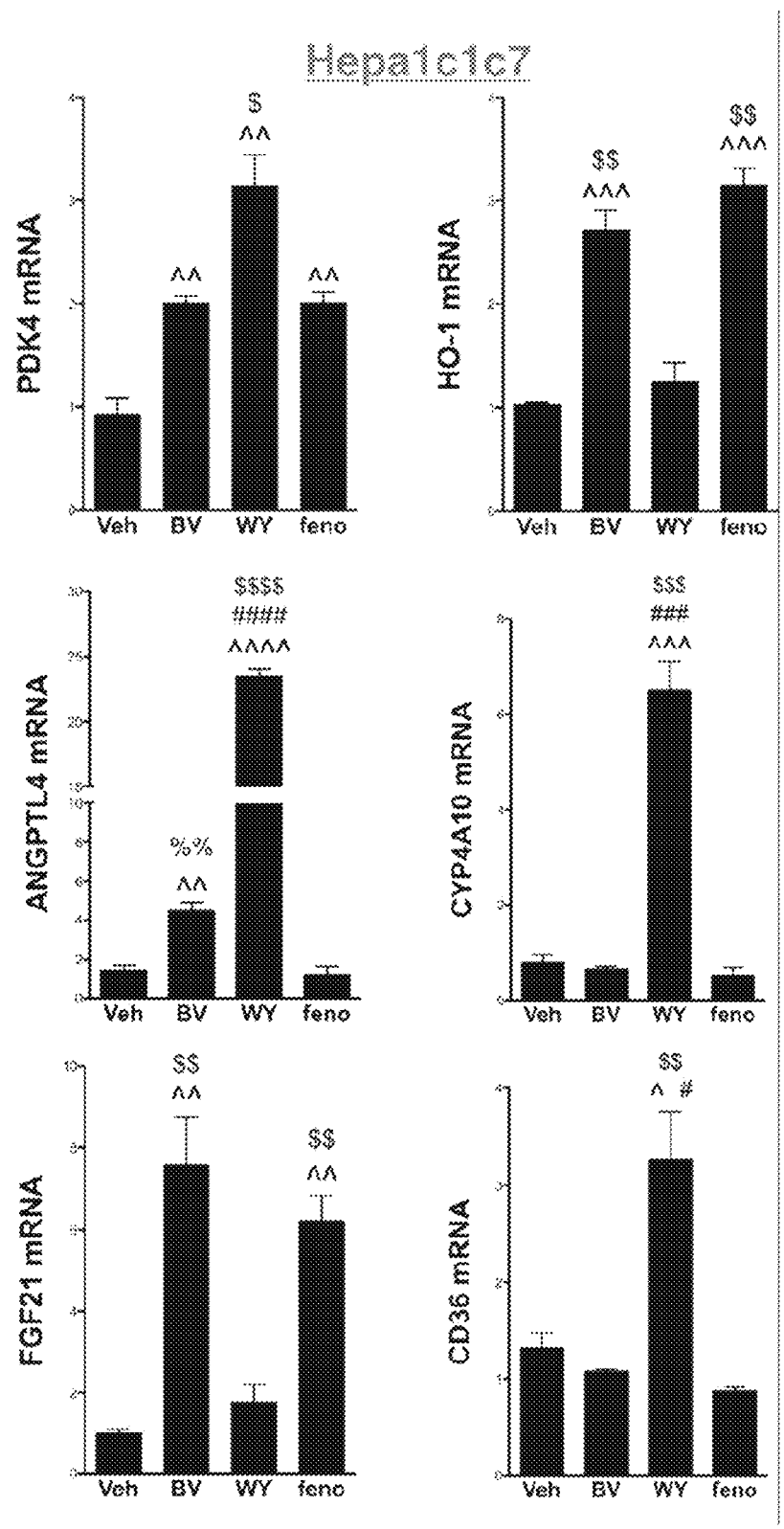

To determine endogenous PPARα gene regulatory activity, vector controls (no PPARα) and PPARα OE 3T3-L1 cells were treated with 50 μM biliverdin, fenofibrate, and WY 14,643 for 24 hours in dialyzed fatty acid-free media. The experiments were conducted with biliverdin because it has greater water solubility than bilirubin, and once inside the cell, it gets rapidly converted to bilirubin via the ubiquitous enzyme biliverdin reductase. In FIG. 4D, it is shown that WY 14,643 strongly induced expression of the anti-diabetic gene, Cluster of Differentiation 36 (CD36). Interestingly, biliverdin significantly ($p<0.05$) increased CD36 mRNA expression more than fenofibrate. PPARα has been shown to increase two major fatty acid oxidation genes, carnitine palmitoyltransferase 1 (CPT1) that is a mitochondrial enzyme that assists in the catalysis of long-chain fatty acids, and the fibroblast growth factor 21 (FGF21), which is a hormone that sensitizes to glucose and reduces adiposity. Biliverdin and fenofibrate increased CPT1 and FGF21 expression more than WY 14,643 treatment, and biliverdin significantly ($p<0.05$) enhanced FGF21 mRNA higher than fenofibrate. To measure known PPARα controlled genes and the response from the different ligands in liver cells, hepa1c1c7 mouse hepatocytes overexpressing PPARα were treated with 50 μM biliverdin, fenofibrate, and WY 14,643 for 24 hours in dialyzed fatty acid-free media (FIG. 4E). The FGF21 and heme oxygenase-1 (HO-1) mRNA response were both increased by biliverdin and fenofibrate, but not with WY 14,643. Pyruvate dehydrogenase kinase 4 (PDK4) expression was increased with all the ligands, but significantly ($p<0.05$) higher with WY 14,643 compared to biliverdin or fenofibrate. Another known PPARα regulated gene, angiopoietin-like 4 (ANGPTL4), which is involved in the release of fat from adipose, was significantly increased by biliverdin ($p=0.0035$) and WY 14,643 ($p<0.0001$), but no response to fenofibrate was observed. Interestingly, CD36 and CYP4A10 mRNA in mouse liver cells only responded to WY 14,643, and not to biliverdin or fenofibrate.

This data indicates that there are variances in PPARα responses with these ligands and that biliverdin/bilirubin may have both anti-diabetic and antilipemic properties. The interaction of ligands with PPARα may be at different binding affinities, which can result in a slight conformational change that can lead to higher regulatory activity of specific genes, possibly by cofactors that bind PPARα at promoters. These small variances can lead to divergent PPARα gene regulation, which has been shown with fenofibrate and WY 14,643. FIGS. 3C, 4D, and 4E show that biliverdin, WY 14,643, and fenofibrate activated PPARα at different levels, which may be due to different ligand binding affinity. Interestingly, the fibrates have been shown to be better at reducing inflammation than WY 14,643 and are typically used in treating inflammatory hyperlipidemia and fatty liver disease. While WY 14,643 does reduce hyperlipidemia, it does not reduce hepatic inflammation. However, WY 14,643 has been shown to be better at reducing blood glucose levels. Because of these differences, PPARα ligands are considered to be either mostly anti-lipidemic or anti-diabetic. Bilirubin may have a similar effect when bound to PPARα and regulate specific gene activity that is both glucose-lowering and antilipemic.

Figure 5A:
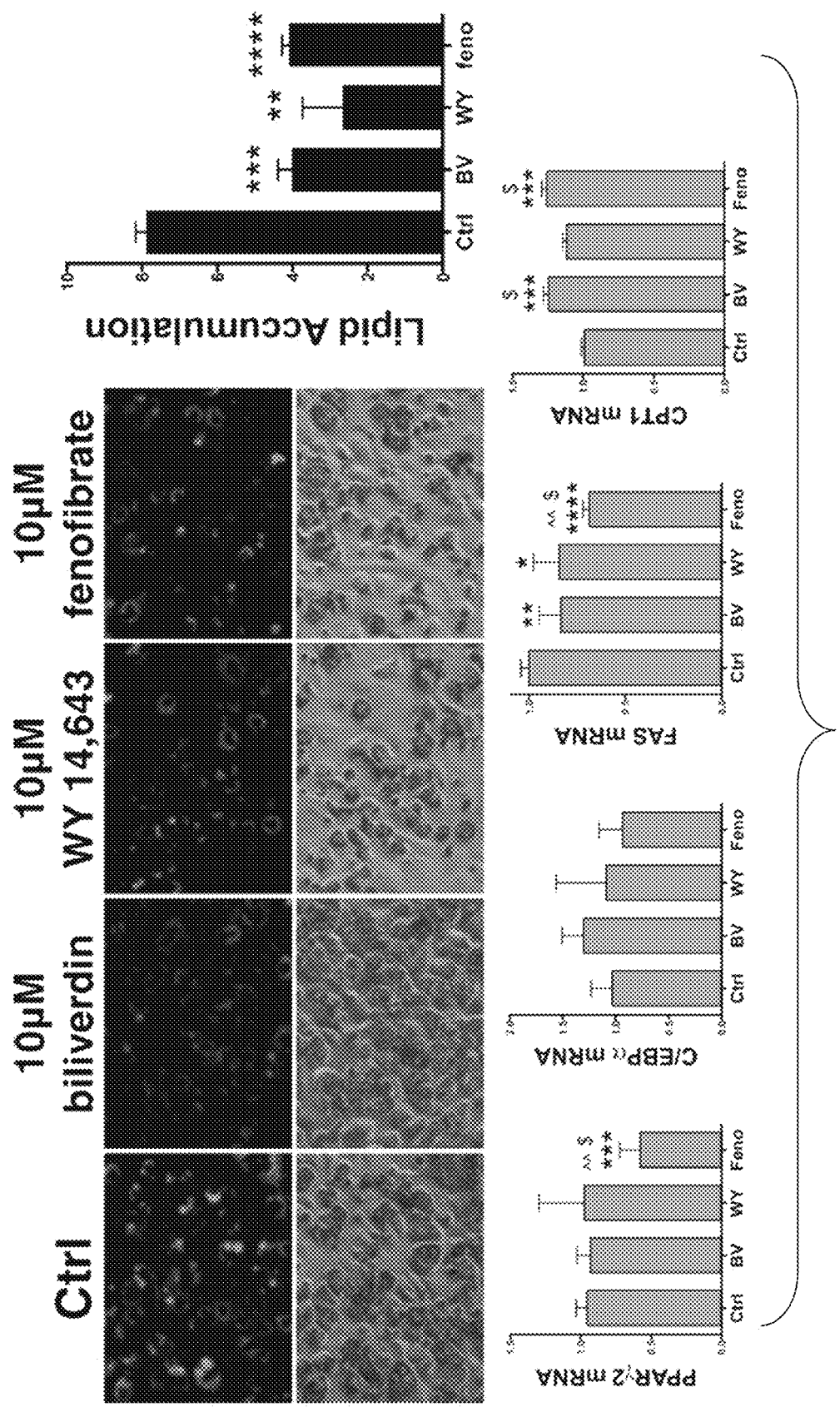
FIGS. 5A-5B: Biliverdin reduces lipid accumulation more than other PPARα ligands. Lipid accumulation was measured by nile red staining (green) and densitometry in 3T3-L1 cells that were differentiated into mature adipocytes treated with vehicle (Ctrl), biliverdin (10 μM), WY 14,643 (10 μM), or fenofibrate (10 μM) over the 9 day protocol and Real-time PCR analysis of PPARγ2, C/EBPα, FAS, and CPT1.
Figure 5B:
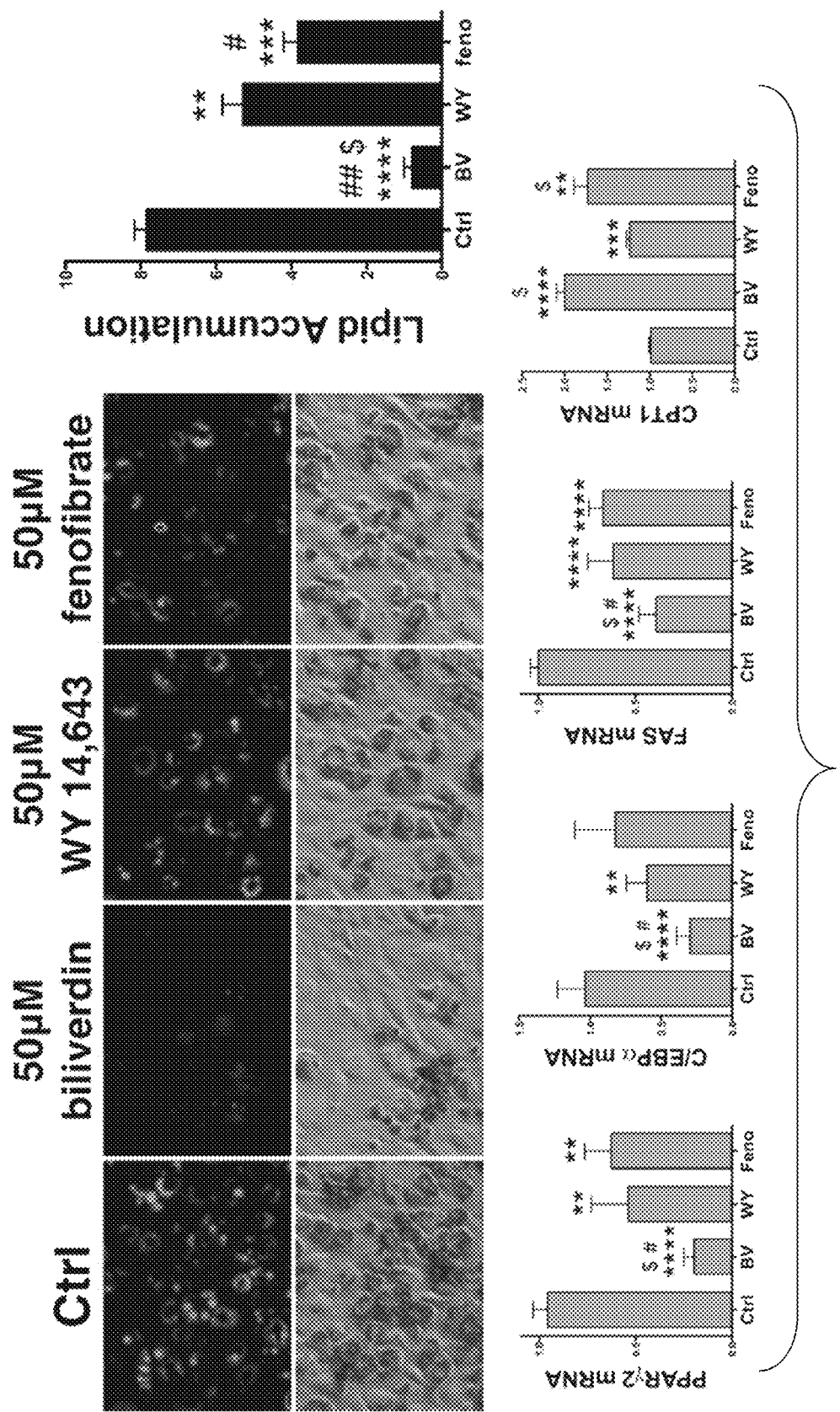

To compare the antilipemic properties of the PPARα ligands, the 3T3-L1 cell model of adipogenesis was used to determine the ligands' effects on lipid accumulation. Treatment of biliverdin (10 μM), WY 14,643 (10 μM), and fenofibrate (10 μM) significantly ($p<0.001$) decreased lipid accumulation during adipogenesis (FIG. 5A). Biliverdin reduced lipid accumulation by 49%, WY 14,643 by 56%, and fenofibrate by 48%. There was no significant difference among the PPARα ligands. PPARα has been previously shown to decrease adiposity by activation of the β-oxidation regulatory gene, CPT. In contrast, rapid loss of fat by leptin increases PPARα expression and fatty acid oxidation genes, and decreases the de novo lipid producing enzyme, fatty acid synthase (FAS). FIG. 5A shows that biliverdin (10 μM), WY 14,643 (10 μM), and fenofibrate (10 μM) significantly ($p<0.001$) decreased expression of FAS. At this concentration, only fenofibrate inhibited expression of PPARγ2. However, both biliverdin and fenofibrate significantly ($p<0.001$) increased expression of CPT1. Treatment with the higher concentration of biliverdin (50 μM), WY 14,643 (50 μM), and fenofibrate (50 μM) significantly ($p<0.001$) decreased lipid accumulation during adipogenesis (FIG. 5B). At the higher doses, biliverdin reduced lipid accumulation by 91%, WY 14,643 by 33%, and fenofibrate by 51%. Interestingly, biliverdin (50 μM) significantly ($P<0.001$) decreased more lipids compared to the same concentration of WY 14,643 and fenofibrate. These results indicate that biliverdin/bilirubin treatment in obese patients has a stronger anti-lipogenic effect. It is also important to note that patients with Gilbert's syndrome typically have about a 50% increased level of bilirubin in their plasma, which equates to 50 μM bilirubin. Large population studies have shown that individuals with serum bilirubin in the upper range of normal to slightly (50-100%) elevated levels are protected against hepatic steatosis, development of diabetes, and the metabolic syndrome. Here, 50 μM bilirubin substantially decreased lipid accumulation in the 3T3-L1 cells, and enhanced PPARα activity at the minimal promoter and endogenous genes.

Figure 6A:
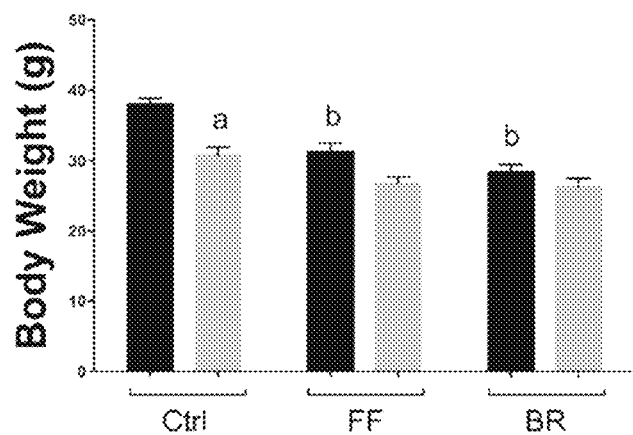
FIG. 6A-6C: Bilirubin reduces body weight and body fat percentage. WT and PPARα KO mice were on a high fat diet for 6 weeks and treated with fenofibrate (FF) or bilirubin (BR) for seven days and body weight (FIG. 6A), percent body fat (FIG. 6B), and lean mass (FIG. 6C) were measured. a, $p<0.05$ (KO versus WT Ctrl); b, $p<0.05$ (WT FF or BR treated versus WT Ctrl) (±S.E.; n=5).
Figure 6B:
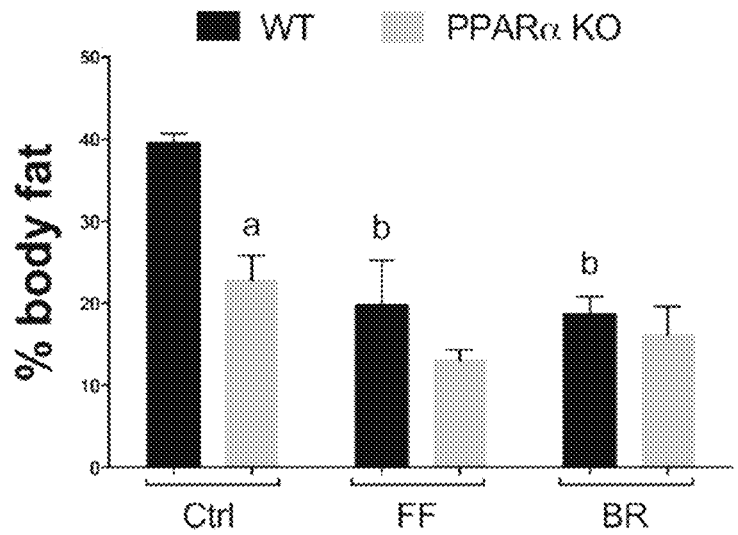
Figure 6C:
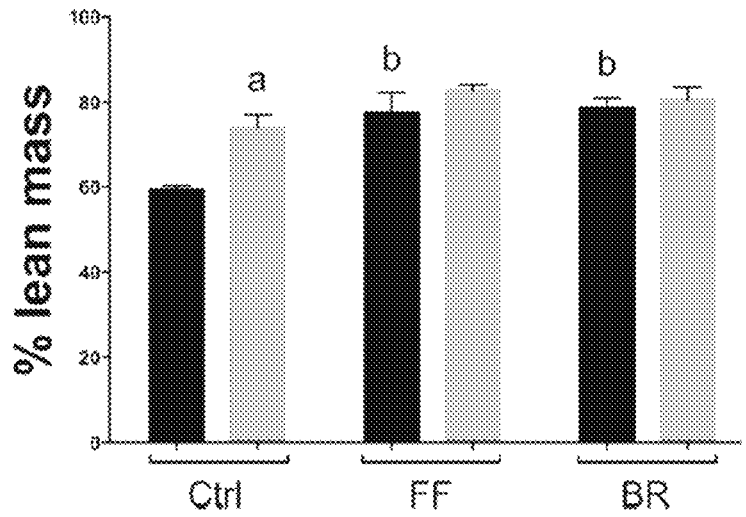
Figure 7A:
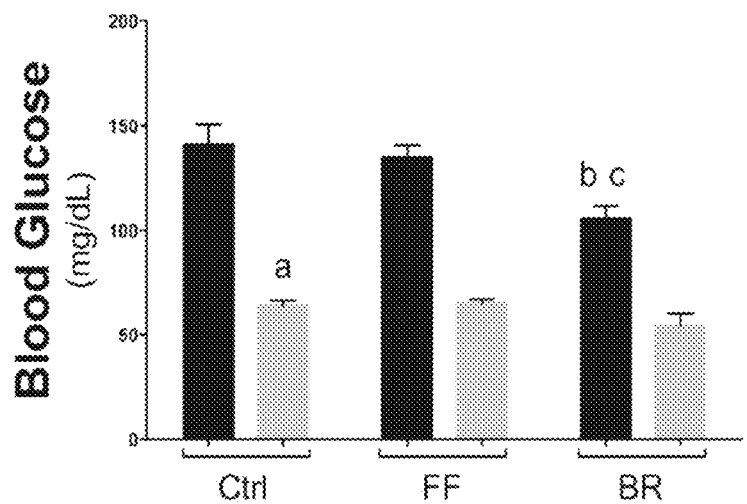
FIGS. 7A-7F: The glucose lowering affect of bilirubin is blunted in PPARα KO mice. WT and PPARα KO mice were on a high fat diet for 6 weeks and treated with fenofibrate (FF) or bilirubin (BR) for seven days and blood glucose (FIG. 7A), plasma insulin (FIG. 7B), alanine aminotransferase (ALT) (FIG. 7C), aspartate aminotransferase (AST) (FIG. 7D), and fibroblast growth factor (FGF21) mRNA in liver (FIG. 7E) and serum levels (FIG. 7F) were measured.
Figure 7B:
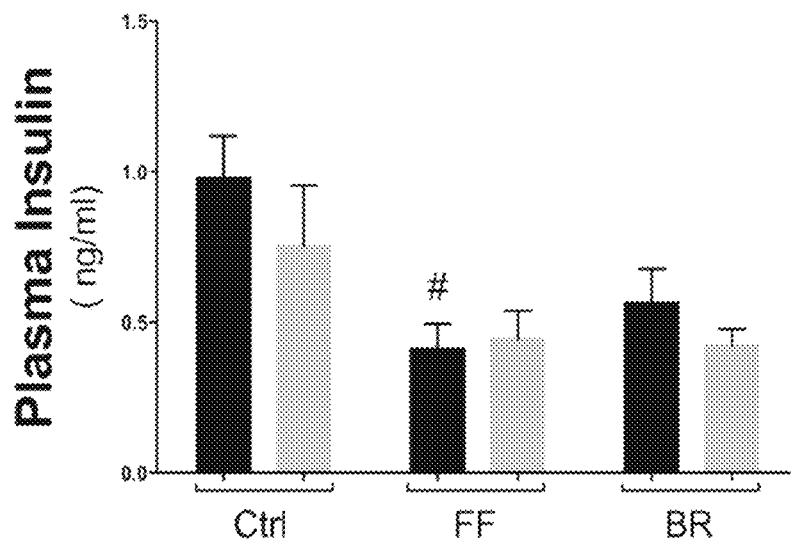
Figure 7C:
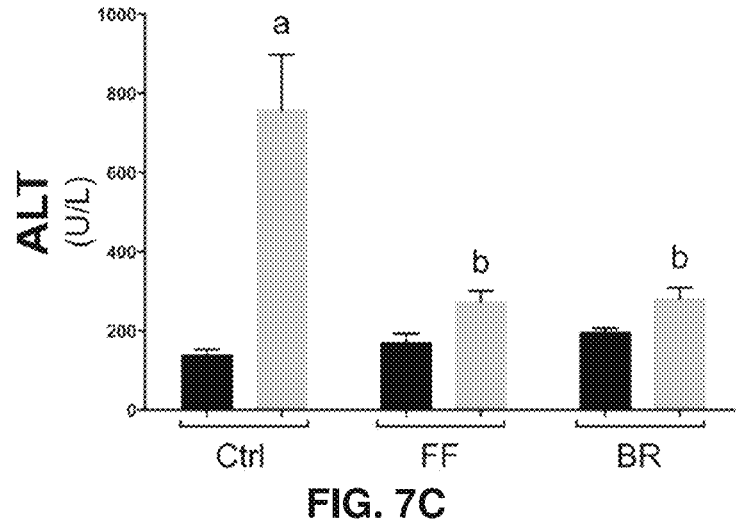
Figure 7D:
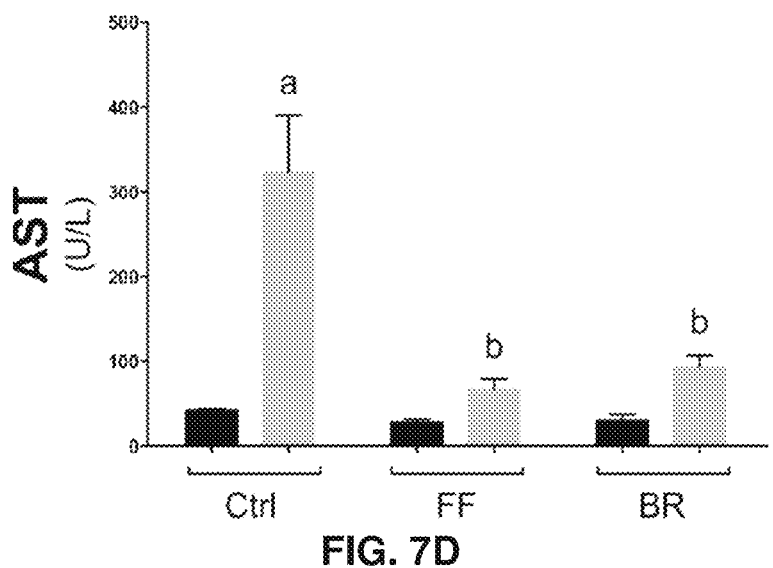
Figure 7E:
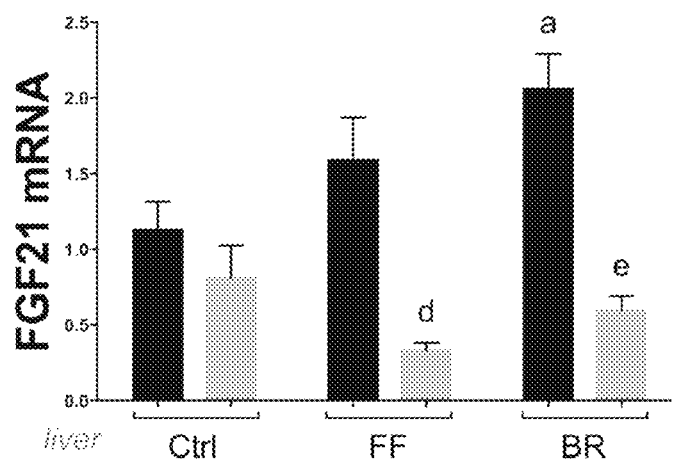
Figure 7F:
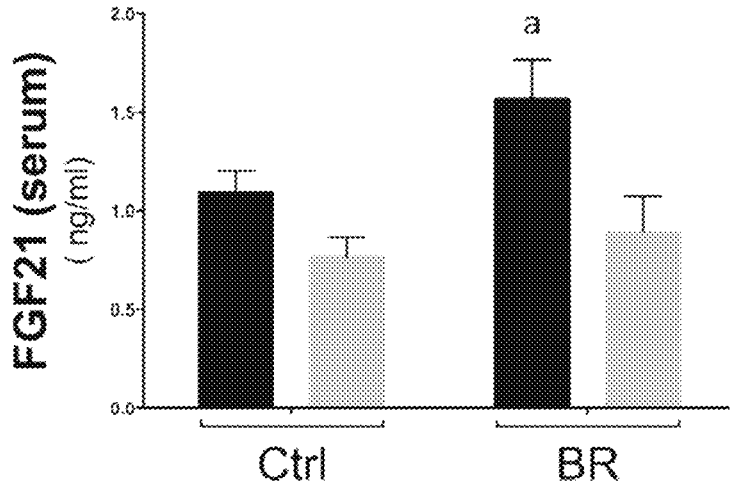

These results show that activation of PPARα in adipocytes increased fatty acid oxidation genes and decreased in de novo lipogenic enzymes. These processes are important in the management of obesity, which has been shown to be reduced with increased bilirubin levels in patients and rodents. Exercise induces fat utilization and burning by enhancing the β-oxidation pathway. Plasma bilirubin levels have been shown to increase with exercise, which may be to induce the burning of fat through PPARα induced βoxidation. In FIG. 6A, it is shown that mice treated with bilirubin (30 mg/kg) and fenofibrate (90 mg/kg) had significantly less body weight. However, bilirubin and fenofibrate had no effect on body weight in PPARα KO mice. The percentage body fat was decreased with fenofibrate and bilirubin, and lean mass was increased, which were not observed in PPARα KO mice (FIGS. 6B & C). Interestingly, bilirubin, but not fenofibrate, reduced blood glucose in the wild-type (WT) mice, and this effect was absent in the PPARα KO mice (FIG. 7A). The plasma insulin levels were reduced with fenofibrate treatment, but not significantly reduced with bilirubin (FIG. 7B). Very high bilirubin levels have been shown in liver damage and failure. However, some reports in Gilbert's patients with slightly elevated bilirubin levels have shown that bilirubin has lipid-lowering and anti-diabetic protective properties. To determine if fenofibrate or bilirubin treatment altered the function of the liver of WT or PPARα KO mice, alanine aminotransferase (ALT) and aspartate aminotransferase (AST) were measured (FIGS. 7C & 7D). ALT and AST are liver enzymes that are released into the bloodstream when it is damaged or diseased. ALT and AST were higher in the control PPARα KO mice, and significantly ($p<0.05$) decreased with bilirubin or fenofibrate treatments. Interestingly, WT mice had no change in AST or ALT with fenofibrate or bilirubin treatments. The ALT and AST levels may have been reduced in the PPARα KO mice by the antioxidant properties of bilirubin, but fenofibrate is not thought to have this property. The glucose lowering effect of bilirubin may be due to the PPARα activation of the FGF21 hormone, which is known to reduce blood glucose and adiposity. Bilirubin significantly ($p=0.05$) enhanced FGF21 mRNA levels in liver (FIG. 7E) and serum (FIG. 7F), but not in PPARα KO mice.

The above shows that bilirubin can bind to enhance PPARα activity, which leads to the increase of lipid burning genes CPT1 and FGF21. Whereas previous studies have only considered bilirubin as an inert antioxidant that does not function to bind transcription factors as a ligand, this data clearly identifies a role for bilirubin as an activator of the nuclear receptor family and opens new drug concepts in the targeting of adiposity and the area or PPARα ligands. The main aspects studied for bilirubin have been on the inhibition of reactive oxygen species with little consideration given to it as a potential signaling molecule. Increased bilirubin levels in humans have already been correlated with reduced adiposity. This example, however, clearly shows that bilirubin has a regulatory role in the mediation of lipid metabolism through PPARα dependent signaling. Without wishing to be bound by theory, it is believed that, given that PPARα regulates genes involved in β-oxidation, increasing bilirubin levels by inhibiting UGTIA1 or by direct treatment has a paramount role in the prevention of obesity. Thus, the bilirubin/PPARα axis is a major signaling paradigm regulating adiposity, which may also attenuate diabetes. Therapeutics inhibiting UGTIA1 may increase plasma bilirubin levels, as well as increase PPARα expression, allowing for the management and prevention of obesity.

Example II—Mouse Model of Hyperbilirubinemia

Increasing production of bilirubin in obese mice has resulted in elevation of PPARα expression and gene-regulatory activity, reducing body weight and blood glucose. Bilirubin may be particularly effective in reducing adiposity as it easily enters the lipid environment, which may serve to protect patients with the metabolic syndrome, as it was shown that higher bilirubin levels were paralleled with lower visceral obesity. This correlated with the observation that obese patients with elevated insulin and visceral adiposity have decreased levels of bilirubin. Therefore, a mouse model of hyperbilirubinemia with Gilbert's mutant UGT1A1*28 allele (HuUGT*28) was tested. The mice were developed in a Ugt1-null background to express the human UDP-glucuronosyltransferase (UGT) 1 locus as a model of humanized Gilbert's Syndrome (hGS). As observed in Gilbert's patients, the hGS mice did have significantly higher plasma bilirubin levels (FIG. 8A). Similar to patient studies, hGS mice have significantly less fat mass and body fat percentage (FIGS. 8B & 8C), as well as an increase in lean mass (FIG. 5D). Importantly, increased bilirubin decreased serum insulin and glucose levels (FIGS. 8E & 8F).

To determine the effect of the elevated bilirubin levels on PPARα in the hGS mice, adipose tissue was immunostained with phospho- and total-PPARα antibodies, and DRAQ5 nuclear stain (FIG. 9). The results show a significant ($p<0.05$) increase in PPARα phosphorylation in the hGS mice.

Example III—Thin Molecules

Cleavage of Bilirubin and Development of the Thin Molecule Library

As shown above, bilirubin functions as a ligand agonist that increases PPARα activity. Data shows that bilirubin (1, FIG. 10) treatment in the presence of PPARα increased the PPARα-regulated promoter PPRE-3tk-luc activity (FIG. 3A), and this binding was direct (FIGS. 2A-2B). However, bilirubin (1) has multiple functions in vivo and does not follow Lipinski's rules for a successful drug candidate. A small molecule scaffold that can be used as a PPARα agonist was identified. The bilirubin compound (1) contains inherent symmetry, and cleavage of bilirubin (1) as shown in FIG. 10 yields products that have some structural similarity to PPARα ligands, namely WY14,643 and the class of compounds known as fenofibrates (FIG. 1).

9-substituted pyrromethenone derivatives have been prepared. These derivatives can be obtained by synthetic methods to cleave bilirubin (1), producing two symmetrical scaffolds. This resulting class of compounds, due to their proposed biological activity (FIG. 10), is referred to as "thin molecules." Regioisomeric mixtures of the thin molecules (2b and 3b, FIG. 10) have been prepared by a diazotization reaction on 1's methylene site followed by nucleophilic displacement with methanol, which is conveniently used as a cosolvent during the reaction. In particular, sodium nitrite and methanol were used to produce 2b and 3b from bilirubin. The skilled person will recognize that the choice of cosolvent for this reaction determines the R group in the resulting thin molecule product. For example, by replacing the methanol cosolvent with ethanol, the thin molecules 2c and 3c can be prepared. By replacing the methanol cosolvent with water, the thin molecules 2a and 3a can be prepared. A library of compounds where the R substitution is dependent on the cosolvent employed is encompassed within the present disclosure. For example, as noted above, ethanol will provide ethoxy isomers 2c1 and 3c, whereas the presence of water will provide alcohols 2a and 3a. *Many substitutions on the 9-pyrrone position can be made.*

Spectroscopic data for regioisomers 2b and 3b is shown in FIG. 11. The proton NMR data, as well as other reported compound characterization, generally agrees with literature precedent for bilirubin. Without wishing to be bound by theory, it is unknown whether just one or both isomers signal through PPARα. Reverse-phased high-performance liquid chromatography (HPLC) enables isolation of each derivative.

To determine if the thin molecules described in FIG. 11 can function as ligands to PPARα, the minimal PPARα promoter, PPRE-3tk-luc, was used to determine if the thin molecules directly increase PPARα activity (FIG. 12). Cos7 cells were transfected with PPARα and RXR and treated with treated with 50 μM of thin molecules, biliverdin, WY 14,643, and control (vehicle). Interestingly, the thin molecules showed a strong induction of PPARα activity (4.4 fold) compared to WY14,643 (2.1 fold), which is known to have high binding affinity to PPARα.

Example IV—Effect of DR Analogs on Adipogenesis

To ascertain the effect of the BR analog (Thin Molecules) Library on adipogenesis, the established murine 3T3-L1 adipocyte differentiation model was employed to demonstrate that biliverdin treatment reduces adiposity. In FIG. 12, it is shown that the BR analogs (Thin Molecules) increased PPARα activity to a greater extent than WY 14,643.

As shown in FIGS. 13A-13B, by using the BR analog mix and treating 3T3-L1 adipocytes, the BR analogs (Thin Molecules) significantly (p<0.01) suppress lipid accumulation at 0.1 µM. While 10 µM biliverdin was required to inhibit lipid accumulation by 50%, FIGS. 13A-13B show that 10 µM BR analogs caused a 10-fold (90%) reduction in lipid accumulation. The best activators of PPARα can then be assessed to determine their dose-dependent action in an adipogenesis assay. For example, using a 9-day differentiation protocol, lipid accumulation can be accessed by Nile red staining, and total RNA can be extracted for the analysis. In brief, gene expression can be measured via Real-time PCR for several known PPARα regulated genes that are anti-diabetic [Glut1, Glut4, and CD36 (pAKT by immunoblotting)] or anti-lipidemic [FGF21, CPT1, and aP2 (pAMPK by immunoblotting)]. The toxicity of the BR analogs can be measured by MTT, to show that there will be differences in PPARα responses with these ligands, low toxicity (similar to bilirubin), and that the BR analogs have both anti-diabetic and anti-lipemic properties similar to bilirubin.

Certain embodiments of the harvesting device and methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A compound comprising Formula A or Formula B:

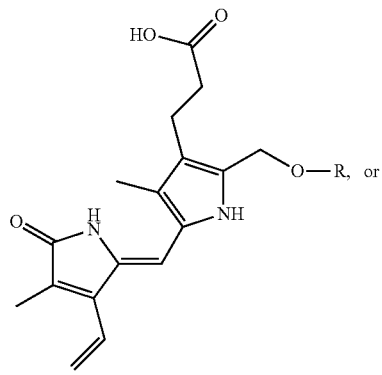

Formula A

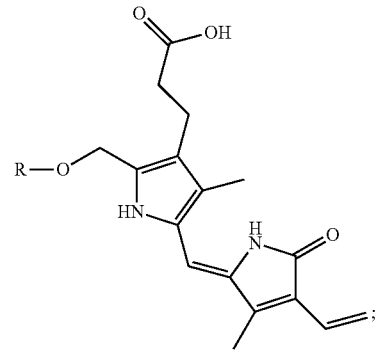

Formula B wherein R is selected from the group consisting of hydrogen and substituted or unsubstituted $C_1$-$C_6$ alkyl; except when R is methyl;
and salts, stereoisomers, racemates, prodrugs, solvates, and hydrates thereof.

2. The compound of claim 1, wherein R is one of ethyl, propyl, butyl, or pentyl.

3. The compound of claim 1, comprising a mixture of Formula A and Formula B.

4. A pharmaceutical composition comprising:
an effective amount of a compound of claim 1; and
a pharmaceutically acceptable carrier, diluent, or adjuvant.

* * * * *